United States Patent
Wolfe et al.

(10) Patent No.: US 11,752,112 B2
(45) Date of Patent: *Sep. 12, 2023

(54) COMPOSITION FOR STIMULATING MUSCLE GROWTH, REPAIR, AND MAINTENANCE

(71) Applicant: The Amino Company LLC, Los Angeles, CA (US)

(72) Inventors: Robert Reese Wolfe, Norwich, CT (US); Frederick Lee Wolfe, Rancho Mirage, CA (US)

(73) Assignee: The Amino Company LLC, Los Angeles, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/666,577

(22) Filed: Feb. 8, 2022

(65) Prior Publication Data

US 2022/0160654 A1      May 26, 2022

Related U.S. Application Data

(62) Division of application No. 16/382,984, filed on Apr. 12, 2019, now Pat. No. 11,241,399.

(51) Int. Cl.
*A61K 31/131*     (2006.01)
*A61K 9/00*       (2006.01)
(Continued)

(52) U.S. Cl.
CPC .......... *A61K 31/131* (2013.01); *A61K 9/0056* (2013.01); *A61K 31/137* (2013.01); *A61K 31/4172* (2013.01); *A23V 2250/06* (2013.01)

(58) Field of Classification Search
None
See application file for complete search history.

(56) References Cited

U.S. PATENT DOCUMENTS 9,597,367 B2    3/2017  Wolfe et al.
2008/0268038 A1*  10/2008  Wolfe ............... A61K 31/60
                                                514/393
(Continued)

FOREIGN PATENT DOCUMENTS

WO   WO-2017059101 A1 *  4/2017  ........... A23L 33/105
WO      2019/035953 A1    2/2019

OTHER PUBLICATIONS

Kreider et al., Effects of Ingesting Supplements Designed to Promote Lean Tissue Accretion on Body Composition During Resistance Training International Journal of Sport Nutrition, 1996, 6, 234-246.

(Continued)

*Primary Examiner* — Kyung S Chang
(74) *Attorney, Agent, or Firm* — Magleby, Cataxinos & Greenwood, P.C.

(57) ABSTRACT

The present invention relates to a composition for stimulating muscle growth, repair and maintenance and the method of using the same. The present invention generally relates to compositions and methods for supporting muscle anabolism. The compositions described herein are pharmaceutical or nutritional compositions suitable for preserving muscle mass, strength, and/or function in a subject in need thereof. The compositions are based on a specially formulated mixture of essential amino acids (EAAs) and protein with additional components. Use of the compositions herein may prevent muscle atrophy associated with periods of rest, such as those following surgery, injury, inactivity and during recovery from disease.

8 Claims, 7 Drawing Sheets

(51) Int. Cl.
*A61K 31/137* (2006.01)
*A61K 31/4172* (2006.01)

(56) References Cited

U.S. PATENT DOCUMENTS

| | | | |
|---|---|---|---|
| 2009/0181903 A1* | 7/2009 | Wolfe | A61K 31/70 514/23 |
| 2010/0267831 A1 | 10/2010 | Kobayashi et al. | |
| 2011/0064720 A1 | 3/2011 | Amato | |
| 2017/0196944 A1 | 7/2017 | Portman | |

OTHER PUBLICATIONS

International Search Report and Written Opinion for International Application No. PCT/US2020/027408, dated Aug. 27, 2020, 12 pages.

* cited by examiner

COMPOSITION FOR STIMULATING MUSCLE GROWTH, REPAIR, AND MAINTENANCE

CROSS-REFERENCE TO RELATED APPLICATION

This application is a divisional of U.S. patent application Ser. No. 16/382,984, filed Apr. 12, 2019, now U.S. Pat. No. 11,241,399, the disclosure of which is hereby incorporated herein in its entirety by this reference.

FIELD OF THE INVENTION

The present invention generally relates to compositions and methods for supporting muscle anabolism. The compositions described herein are pharmaceutical or nutritional compositions suitable for preserving muscle mass, strength, and/or function in a subject in need thereof. The compositions are based on a specially formulated mixture of essential amino acids (EAAs) and protein with additional components. Use of the compositions herein may prevent muscle atrophy associated with periods of rest, such as those following surgery, injury, inactivity and during recovery from disease.

BACKGROUND OF THE INVENTION

Muscle protein is in a constant state of turnover, meaning muscle protein is being broken down and synthesized continuously. The metabolic basis of muscle anabolism, defined herein as an increase in muscle mass and/or strength, is the circumstance and/or circumstances in which the rate of muscle protein synthesis exceeds the rate of muscle protein breakdown. The same processes apply to whole body protein anabolism. Muscle protein turnover constitutes between 30%-40% of whole-body protein turnover. Conversely, loss of muscle and whole-body protein is called catabolism. Catabolism of body proteins, including muscle is a primary component of the metabolic response to stress and injury which is characterized by whole-body protein loss, mainly reflecting increased net breakdown of muscle proteins. Muscle wasting and weakness associated the metabolic response to stress and injury may adversely affect an afflicted subject's outcome owing to delayed ambulation and involvement of respiratory muscles, as well as delayed wound healing. Accordingly, there is a need for effective formulations, and especially nutritional formulations, that help prevent increases in the breakdown of body proteins, especially muscle proteins, during these periods.

To generate new muscle proteins, precursor amino acids for the synthesis of new muscle proteins are derived from the process of protein breakdown, or, in the case of non-essential amino acids (NEAAs), from de novo synthesis in the body. There are 9 essential amino acids (EAAs) that are components of body proteins that cannot be produced in the body—leucine, isoleucine, valine, histidine, threonine, phenylalanine, lysine, methionine, and tryptophan. Accordingly, the amount of EAAs available for re-incorporation into muscle protein is rate limiting for muscle protein synthesis, since EAAs cannot be produced in the body. Since some EAAs released in the process of protein breakdown are oxidized, they are not available to be reincorporated into body protein. As such, the pool of EAAs available for re-incorporation into muscle protein is further limited and must be supported by dietary intake.

The notion that a minimal amount of each EAA is required to maintain an overall balance between protein synthesis and breakdown has led to the development of dietary supplements of EAAs to promote muscle anabolism. Such formulations provide a mixture of all 9 EAAs under the presumption that the minimal dietary requirements needed to supply sufficient EAAs for maximal muscle protein synthesis are not met with a normal diet. Further, these formulations typically provide a disproportionately high amount of the EAA leucine on the assumption that leucine plays an unique regulatory role in addition to being a component of body proteins. However, while an excessive amount of leucine in a composition of EAAs may be of benefit in some circumstances, a disproportionate amount of leucine by necessity limits the proportions the other EAAs in the formulations. In many circumstances this will make an EAA other than leucine rate-limiting for protein synthesis. Under most circumstance a composition containing only sufficient leucine to satisfy requirements for precursor availability, with corresponding increased proportions of the other EAAs, will be superior to a formulation containing 35-40% or more leucine. Therefore, there is a need in the art for compositions comprising a unique combination of ingredients specifically designed for maximal stimulation of muscle protein synthesis under most conditions, including recovery from stresses such as surgery, injury or disease. Such compositions comprise a combination of ingredients that account for the limiting step in protein synthesis which is the intracellular availability of EAA precursors of protein in proportion to the profile of EAAs that comprise body proteins.

received a nutritionally balanced diet meeting all known nutritional requirements in three meals per day, 5 hours apart, and the experimental group (EAA) also consumed three doses of 16.5 grams essential amino acids and 30 grams carbohydrate 5 hours apart. Error bars represent standard error of mean (SE) assessed via a standard student t-test.

Figure 5:
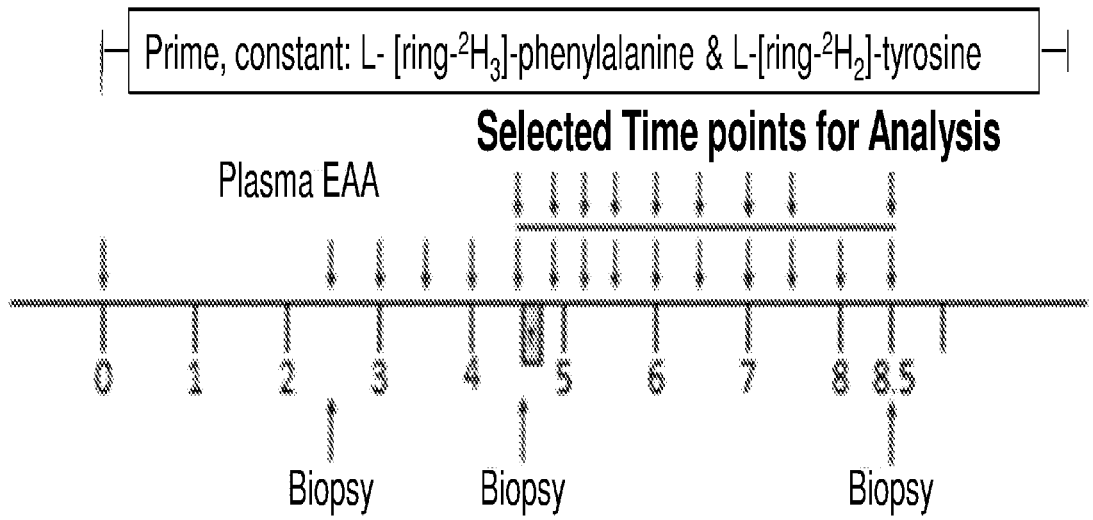

FIG. 5 depicts a schematic showing the isotope infusion protocol for the study assessing the response of whole-body protein synthesis and breakdown in the basal state and following consumption of one of two doses of the composition described herein or one dose of whey protein.

Figure 6:
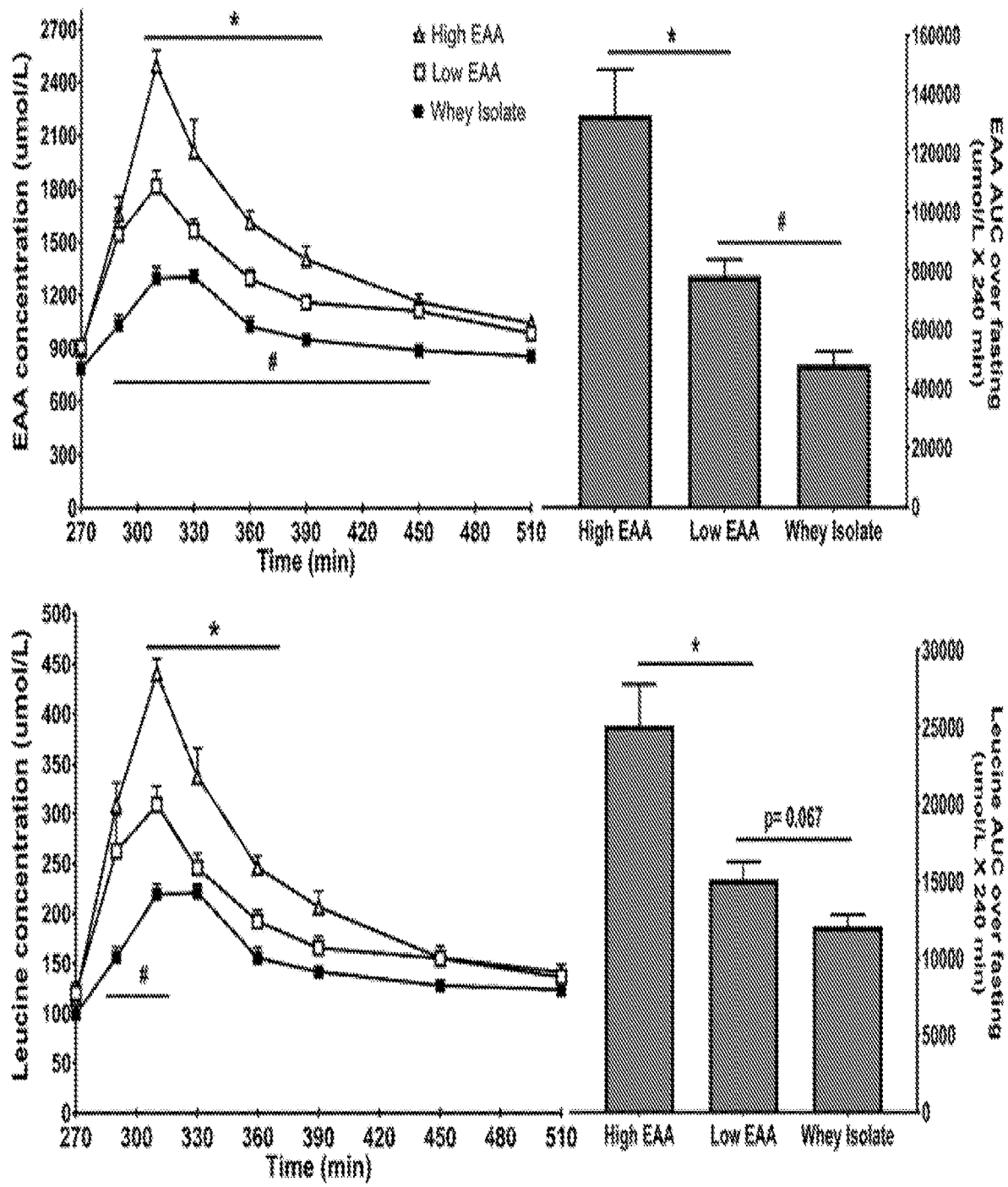

FIG. 6. Depicts a graph of the time course response of plasma essential amino acid (EAA) and leucine concentrations following the consumption of High EAA (12.6 g EAAs+protein), Low EAA (6.3 g EAAs+protein), and the whey isolate product (12.6 g of Gatorade Recover Whey Protein). There were significant effects for treatment, time and interaction between treatment and time for EAA and Leucine. The symbol "*" represents that High EAA is significantly higher than Low EAA (p<0.01) and "#" represents significant differences between Low EAA and Whey (p<0.01). Values (n=8) are expressed as mean±SEM.

Figure 7:
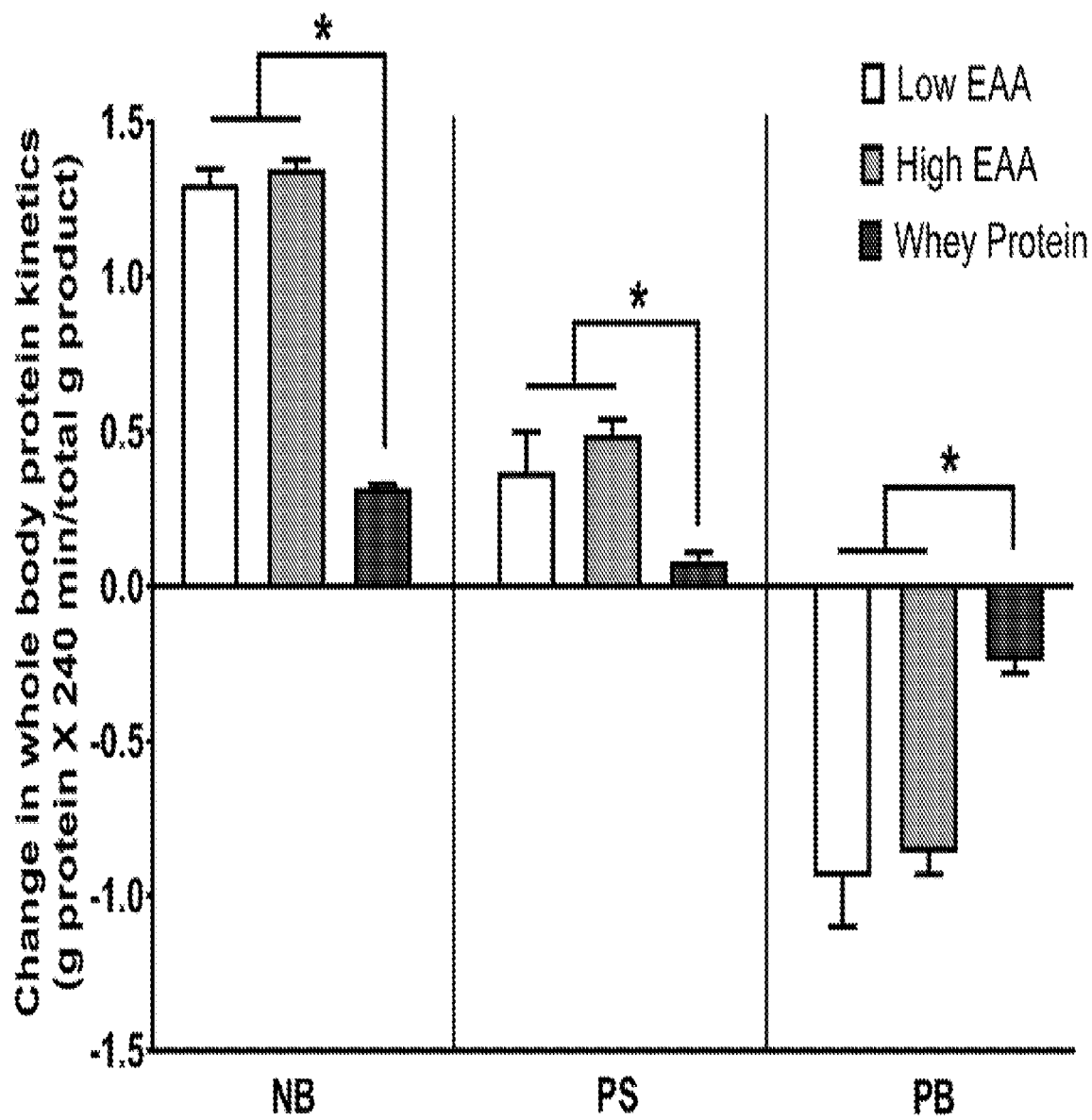

FIG. 7 depicts a graph showing changes in whole body protein kinetics in subjects for the four 4 hours after consumption either a low dose (6.3 g) of an essential amino acid (EAA)/protein mixture, a high dose of an EAA/protein mixture (12.6 g), or whey protein product (12.6 g). Values are change from the basal (post-absorptive) state. Error bars represent standard error of mean (SE) assessed via ANOVA.

DETAILED DESCRIPTION OF THE INVENTION

Current compositions to promote or preserve muscle anabolism presume minimal dietary requirements for EAAs are met with the normal diet and have proven ineffective in preservation of muscle mass and strength in circumstances in which losses would normally occur, such following surgery, injury, and/or inactivity. Importantly, the present disclosure provides compositions comprised of a combination of ingredients directed toward maximal stimulation of protein synthesis under most conditions, including but not limited to recovery from stresses such as surgery, injury, or disease, as detailed below. In general, the compositions disclosed herein may comprise one or more amino acids. In various embodiments, compositions of the present disclosure comprise one or more essential amino acids (EAAs). In various embodiments, compositions of the present disclosure comprise one or more essential amino acids (EAAs) and one or more non-essential amino acids (NEAAs). In some embodiments, compositions of the present disclosure increase protein synthesis. In other embodiments, compositions of the present disclosure promote anabolism. In yet other embodiments, compositions of the present disclosure preserve muscle mass and/or strength. In still other embodiments, compositions of the present disclosure prevent muscle atrophy.

(I) Compositions

One aspect of the present disclosure encompasses a composition comprising one or more amino acids. These amino acids can comprise one or more essential amino acids (EAAs). A composition disclosed herein may further comprise one or more non-essential amino acids (NEAAs). A composition disclosed herein may further comprise one or intact proteins. A composition disclosed herein may further comprise one or more nutrient elements. A composition disclosed herein may further comprise one or more excipients.

(a) Amino Acids

In various embodiments, compositions disclosed herein may comprise at least one or more amino acids. As used herein, "amino acids" are represented by their full name, their three letter code, or their one letter code as well known in the art. Amino acid residues are abbreviated as follows: Phenylalanine is Phe or F; Leucine is Leu or L; Isoleucine is Ile or I; Methionine is Met or M; Valine is Val or V; Serine is Ser or S; Proline is Pro or P; Threonine is Thr or T; Alanine is Ala or A; Tyrosine is Tyr or Y; Histidine is His or H; Glutamine is Gln or Q; Asparagine is Asn or N; Lysine is Lys or K; Aspartic Acid is Asp or D; Glutamic Acid is Glu or E; Cysteine is Cys or C; Tryptophan is Trp or W; Arginine is Arg or R; and Glycine is Gly or G. An amino acid as disclosed herein may be either naturally or non-naturally occurring. As used herein, a "naturally occurring amino acid" is one that has the general core structure

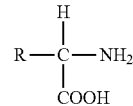

and that is synthesized in nature. Examples of naturally occurring amino acids that may be used in the present invention include, but are not limited to, alanine, arginine, asparagine, aspartic acid, carnitine, cysteine, glutamine, glutamic acid, glycine, citrulline, histidine, isoleucine, leucine, lysine, methionine, phenylalanine, proline, serine, threonine, tryptophan, tyrosine, and derivatives, analogs, and combinations thereof. The present invention may include levorotary (L) stereoisomers of such amino acids.

As used herein, a "non-naturally occurring amino acid" may be an analog derivative and/or enantiomer of a naturally occurring amino acid. The term "non-naturally occurring amino acid" includes, but is not limited to, amino acids that occur naturally by modification of a naturally encoded amino acid (including but not limited to, the 20 naturally occurring amino acids contained in body proteins or pyrrolysine and selenocysteine) but are not themselves incorporated into a growing polypeptide chain by the translation complex. Non-limiting examples of non-naturally occurring amino acids that may be used in the present invention include L-hydroxypropyl, L-3,4-dihydroxyphenylalanyl, alpha-amino acids such as L-alpha-hydroxylysyl and D-alpha-methylalanyl, L-alpha-methylalanyl, beta-amino acids, N-acetylglucosaminyl-L-serine, N-acetylglucosaminyl-L-threonine, O-phosphotyrosine, and isoquinolyl.

As used herein, the term "amino acid" may also encompass chemically modified amino acids, including but not limited to salts, amino acid derivatives (such as amides), and substitutions. Amino acids contained within the compositions of the present invention can be modified by methylation, amidation, acetylation or substitution with other chemical groups. In various embodiments, amino acids used in compositions disclosed herein may be produced by any fermentation method known in the art. In other embodiments, amino acids used in compositions disclosed herein may be produced by any hydrolysis method known in the art. In preferred embodiments, amino acids used in compositions disclosed herein may be of food grade quality or pharmaceutical grade quality.

In various embodiments, amino acids used in compositions disclosed herein may comprise one or more essential amino acids (EAAs). As used herein, "essential amino acids" are amino acids that are components of body proteins that cannot be made by the body of a subject. EAAs suitable for compositions disclosed herein may comprise one or more free EAAs, one or more EAA derivatives thereof, or one or more EAA precursors thereof. In various embodiments, a composition disclosed herein may comprise about 80% to about 85% total EAAs by total weight of the composition. In yet other embodiments, compositions may comprise about 80%, about 80.5%, about 81%, about 81.5%, about 82%, about 82.5%, about 83%, about 83.5%, about 84%, about 84.5%, or about 85% total EAAs by total weight of the composition.

In embodiments in which the composition comprises one or more EAAs, EAAs may be but are not limited to histidine, isoleucine, leucine, lysine, methionine, phenylalanine, threonine, tryptophan, and valine or their hydroxy analogs. In various embodiments, EAAs used in compositions disclosed herein may comprise one or more of histidine, isoleucine, leucine, lysine, methionine, phenylalanine, valine, and threonine. In other embodiments, compositions may comprise two or more EAAs selected from the group comprising histidine, isoleucine, leucine, lysine, methionine, phenylalanine, valine, and threonine. In yet other embodiments, compositions may comprise three or more EAAs selected from the group comprising histidine, isoleucine, leucine, lysine, methionine, phenylalanine, valine, and threonine. In still other embodiments, compositions may comprise four or more EAAs selected from the group comprising histidine, isoleucine, leucine, lysine, methionine, phenylalanine, valine, and threonine. In other embodiments, compositions may comprise five or more EAAs selected from the group comprising histidine, isoleucine, leucine, lysine, methionine, phenylalanine, valine, and threonine. In yet other embodiments, compositions may comprise six or more EAAs selected from the group comprising histidine, isoleucine, leucine, lysine, methionine, phenylalanine, valine, and threonine. In still other embodiments, compositions may comprise seven or more EAAs selected from the group comprising histidine, isoleucine, leucine, lysine, methionine, phenylalanine, valine, and threonine. In preferred embodiments, compositions may comprise histidine, isoleucine, leucine, lysine, methionine, phenylalanine, valine, and threonine. In yet other embodiments, compositions disclosed herein may not be supplemented with tryptophan. In other embodiments, compositions disclosed herein may comprise limited amounts of leucine. In still other embodiments, compositions disclosed herein may comprise limited amounts of leucine and may not be supplemented with tryptophan. In yet other embodiments, compositions disclosed herein may comprise a higher proportion of threonine than in the profile of requirements for EAAs currently known in the art.

In other embodiments, a composition comprising histidine may comprise about 8% to about 12% histidine by weight of total EAAs weight of the composition. In other embodiments, a composition comprising histidine may comprise about 8%, about 8.5%, about 9%, about 9.5%, about 10%, about 10.5%, about 11%, about 11.5%, or about 12% histidine by weight of total EAAs weight of the composition. In preferred embodiments, a composition comprising histidine may comprise about 8% to about 12% L-histidine by weight of total EAAs weight of the composition. In other embodiments, a composition comprising histidine may comprise about 4% to about 6% histidine by total weight of the composition. In other embodiments, a composition comprising histidine may comprise about 4%, about 4.5%, about 5%, about 5.5%, or about 6% histidine by total weight of the composition.

In other embodiments, a composition comprising isoleucine may comprise about 9% to about 11% isoleucine by weight of total EAAs weight of the composition. In other embodiments, a composition comprising isoleucine may comprise about 9%, about 9.5%, about 10%, about 10.5%, or about 11% isoleucine by weight of total EAAs weight of the composition. In preferred embodiments, a composition comprising isoleucine may comprise about 9% to about 11% L-isoleucine by weight of total EAAs weight of the composition. In other embodiments, a composition comprising isoleucine may comprise about 4.5% to about 5.5% isoleucine by total weight of the composition. In other embodiments, a composition comprising isoleucine may comprise about 4.5%, about 5%, or about 5.5% isoleucine by total weight of the composition.

In other embodiments, a composition comprising leucine may comprise about 18% to about 22% leucine by weight of total EAAs weight of the composition. In other embodiments, a composition comprising leucine may comprise about 18%, about 18.5%, about 19%, about 19.5%, about 20%, about 20.5%, about 21%, about 21.5%, or about 22% leucine by weight of total EAAs weight of the composition. In preferred embodiments, a composition comprising leucine may comprise about 18% to about 22% L-leucine by weight of total EAAs weight of the composition. In other embodiments, a composition comprising leucine may comprise about 9% to about 11% leucine by total weight of the composition. In other embodiments, a composition comprising leucine may comprise about 9%, about 9.5%, about 10%, about 10.5%, or about 11% leucine by total weight of the composition.

In other embodiments, a composition comprising lysine may comprise about 16% to about 20% lysine by weight of total EAAs weight of the composition. In other embodiments, a composition comprising lysine may comprise about 16%, about 16.5%, about 17%, about 17.5%, about 18%, about 18.5%, about 18%, about 18.5%, about 19%, about 19.5%, or about 20% lysine by weight of total EAAs weight of the composition. In some preferred embodiments, a composition comprising lysine may comprise about 16% to about 20% L-lysine by weight of total EAAs weight of the composition. In other preferred embodiments, a composition comprising lysine may comprise about 16% to about 20% L-lysine hydrochloride by weight of total EAAs weight of the composition. In some embodiments, a composition comprising lysine may comprise about 7% to about 9% lysine by total weight of the composition. In other embodiments, a composition comprising lysine may comprise about 7%, about 7.5%, about 8%, about 8.5%, or about 9% lysine by total weight of the composition.

In other embodiments, a composition comprising methionine may comprise about 2% to about 5% methionine by weight of total EAAs weight of the composition. In other embodiments, a composition comprising methionine may comprise about 2%, about 2.5%, about 3%, about 3.5%, about 4%, about 4.5%, or about 5% methionine by weight of total EAAs weight of the composition. In preferred embodiments, a composition comprising methionine may comprise about 2% to about 5% L-methionine by weight of total EAAs weight of the composition. In other embodiments, a composition comprising methionine may comprise about 1% to about 2.5% methionine by total weight of the composition. In other embodiments, a composition comprising methionine may comprise about 1%, about 1.5%, about 2%, or about 2.5% methionine by total weight of the composition.

In other embodiments, a composition comprising phenylalanine may comprise about 10% to about 14% phenylalanine by weight of total EAAs weight of the composition. In other embodiments, a composition comprising phenylalanine may comprise about 10%, about 10.5%, about 11%, about 11.5%, about 12%, about 12.5%, about 13%, about 13.5%, and to about 14%. by weight of total EAAs of the composition. In preferred embodiments, a composition comprising phenylalanine may comprise about 12% to about 14% L-phenylalanine by weight of total EAAs weight of the composition. In other embodiments, a composition comprising phenylalanine may comprise about 6% to about 8% phenylalanine by total weight of the composition. In other embodiments, a composition comprising phenylalanine may comprise about 6%, about 6.5%, about 7%, about 7.5%, or about 8% phenylalanine by total weight of the composition.

In other embodiments, a composition comprising valine may comprise about 9% to about 12% valine by weight of total EAAs weight of the composition. In other embodiments, a composition comprising valine may comprise about 9%, about 9.5%, about 10%, about 10.5%, about 11%, about 11.5%, or about 12% valine by weight of total EAAs weight of the composition. In preferred embodiments, a composition comprising valine may comprise about 9% to about 12% L-valine by weight of total EAAs weight of the composition. In other embodiments, a composition comprising valine may comprise about 4.5% to about 6% valine by total weight of the composition. In other embodiments, a composition comprising valine may comprise about 4.5%, about 5%, about 5.5%, or about 6.5% valine by total weight of the composition.

In other embodiments, a composition comprising threonine may comprise about 14% to about 19% threonine by weight of total EAAs weight of the composition. In other embodiments, a composition comprising threonine may comprise about 14%, about 14.5%, 15%, about 15.5%, about 16%, about 16.5%, about 17%, about 17.5%, about 18%, about 18.5% or about 19% threonine by weight of total EAAs weight of the composition. In preferred embodiments, a composition comprising threonine may comprise about 14% to about 19% L-threonine by weight of total EAAs weight of the composition. In other embodiments, a composition comprising threonine may comprise about 7% to about 9% threonine by total weight of the composition. In other embodiments, a composition comprising threonine may comprise about 7%, about 7.5%, about 8%, about 8.5%, or about 9% threonine by total weight of the composition.

In still other embodiments, a composition comprising threonine may comprise a disproportionately high amount of threonine over standard dietary requirements. In some aspects, the amount of threonine comprising a composition disclosed herein is more than about 1%, less than about 2%, less than about 4%, less than about 6%, less than about 10%, less than about 20%, or less than about 30% of the dietary requirement for threonine known in the art at the time of invention.

In various embodiments, a composition may comprise about 8 to about 12% histidine by weight of total EAAs weight of the composition, about 9% to about 11% isoleucine by weight of total EAAs weight of the composition, about 16% to about 20% lysine by weight of total EAAs weight of the composition, about 2% to about 5% methionine by weight of total EAAs weight of the composition, about 12% to about 16% phenylalanine by weight of total EAAs weight of the composition, about 9% to about 12% valine by weight of total EAAs weight of the composition, about 14% to about 19% threonine by weight of total EAAs weight of the composition, and about 18% to about 22% leucine by weight of total EAAs weight of the composition. In other embodiments, a composition may not comprise tryptophan but may comprise about 8 to about 12% histidine by weight of total EAAs weight of the composition, about 9% to about 11% isoleucine by weight of total EAAs weight of the composition, about 16% to about 20% lysine by weight of total EAAs weight of the composition, about 2% to about 5% methionine by weight of total EAAs weight of the composition, about 12% to about 16% phenylalanine by weight of total EAAs weight of the composition, about 9% to about 12% valine by weight of total EAAs weight of the composition, about 14% to about 19% threonine by weight of total EAAs weight of the composition, and about 18% to about 22% leucine by weight of total EAAs weight of the composition.

In other embodiments, a composition may comprise about 4% to about 6% histidine by weight of the composition, about 4.5% to about 5.5% isoleucine by weight of the composition, about 8% to about 10% lysine by weight of the composition, about 1% to about 2.5% methionine by weight of the composition, about 6% to about 8% phenylalanine by weight of the composition, about 4.5% to about 6% valine by weight of the composition, about 7% to about 9% threonine by weight of the composition, and about 9% to about 11% leucine by weight of the composition. In other embodiments, a composition may not comprise tryptophan but may comprise about 4% to about 6% histidine by weight of the composition, about 4.5% to about 5.5% isoleucine by weight of the composition, about 8% to about 10% lysine by weight of the composition, about 1% to about 2.5% methionine by weight of the composition, about 6% to about 8% phenylalanine by weight of the composition, about 4.5% to about 6% valine by weight of the composition, about 7% to about 9% threonine by weight of the composition, and about 9% to about 11% leucine by weight of the composition.

In preferred embodiments, a composition may comprise about 10% histidine, about 10% isoleucine, about 19% lysine, about 3% methionine, about 12% phenylalanine, about 10% valine, about 16% threonine, and about 20% leucine by weight of total EAAs.

In various embodiments, amino acids used in compositions disclosed herein may comprise non-essential amino acids (NEAAs). As used herein, "non-essential amino acids" are those amino acids that are synthesized from by the body of a subject. NEAAs suitable for compositions disclosed herein may comprise one or more free NEAAs, one or more NEAA derivatives thereof, or one or more NEAA precursors thereof. In various embodiments, NEAAs suitable for compositions disclosed herein are within one or more dietary proteins. In various embodiments, a composition disclosed herein may comprise about 15% to about 20% total NEAAs by total weight of the composition. In other embodiments, a composition may comprise about 15%, about 15.5%, about 16%, about 16.5%, about 17%, about 17.5%, about 18%, about 18.5%, about 19%, about 19.5%, about 20% total NEAAs by total weight of the composition.

In embodiments in which the composition comprises one or more NEAAs, NEAAs may be but are not limited to alanine, asparagine, aspartic acid, and glutamic acid or their derivatives and precursors thereof. In various embodiments, NEAAs used in compositions disclosed herein may comprise one or more precursors of arginine. In an aspect, a precursor of arginine suitable for the compositions disclosed herein may be citrulline.

In other embodiments, a composition disclosed herein may comprise about 8% to about 12% citrulline by total free amino acids. In still other embodiments, a composition disclosed herein may comprise about 8%, about 8.5%, about 9%, about 9.5%, about 10%, about 10.5%, about 11%, about 11.5%, or about 12% citrulline by total weight of the free amino acids. In various embodiments, a composition disclosed herein comprising citrulline may comprise about 3.5%, about 4.0%, about 4.5%, about 5.0%, about 5.5%, about 6.0%, about 6.5%, about 7.0%, about 7.5%, about 8.0%, about 8.5%, about 9.0%, about 9.5%, about 10.0%, about 10.5%, about 11.0%, about 11.5%, about 12.0%, about 12.5%, about 13.0%, about 13.5%, about 14.0%, about 14.5%, about 15.0%, about 15.5%, about 16.0%, about 16.5%, about 17.0%, about 17.5%, about 18.0%, or about 18.5% citrulline by total weight of the composition.

In various embodiments, NEAAs used in compositions disclosed herein may comprise one or more derivatives of NEAAs. In an aspect, a derivative of NEAAs may be synthesized from one or more NEAAs. In another aspect, a NEAA synthesized from one or more NEAAs suitable for the compositions disclosed herein may be creatine. In a preferred embodiment, compositions disclosed herein comprise creatine monohydrate.

In various embodiments, a composition disclosed herein may comprise one or more EAAs and creatine (a NEAA) in an amount sufficient to increase protein synthesis compared to a composition consisting of EAAs. In various embodiments, a composition disclosed herein may comprise one or more EAAs and creatine in an amount sufficient to increase protein synthesis by at least 2-fold, at least 4-fold, or at least 5-fold more than a composition consisting of EAAs. In the embodiments, a composition disclosed herein may comprise about 5% to about 10% creatine by total weight of the free amino acids. In other embodiments, a composition disclosed herein may comprise about 5%, about 5.5%, about 6%, about 6.5.%, about 7%, about 7.5%, about 8%, about 8.5%, about 9%, about 9.5%, or about 10% creatine by total weight of the free amino acids in the composition. In various embodiments, a composition disclosed herein comprising creatine may comprise about 3.5% to about 18.5% creatine by total weight of the composition. In other embodiments, a composition disclosed herein comprising creatine may comprise about 3.5%, about 4.0%, about 4.5%, about 5.0%, about 5.5%, about 6.0%, about 6.5%, about 7.0%, about 7.5%, about 8.0%, about 8.5%, about 9.0%, about 9.5%, about 10.0%, about 10.5%, about 11.0%, about 11.5%, about 12.0%, about 12.5%, about 13.0%, about 13.5%, about 14.0%, about 14.5%, about 15.0%, about 15.5%, about 16.0%, about 16.5%, about 17.0%, about 17.5%, about 18.0%, or about 18.5% citrulline by total weight of the composition.

In various embodiments, compositions disclosed herein may comprise at least one or more EAAs and at least one or more NEAAs. In other embodiments, compositions comprise about 15% NEAAs and about 85% EAAs, about 16% NEAAs and about 84% EAAs, about 17% NEAAs and about 83% EAAs, about 18% NEAAs and about 82% EAAs, about 19% NEAAs and about 81% EAAs, or about 20% NEAAs and about 85% EAAs by weight of total weight of the composition.

(b) Intact Proteins

In various embodiments, a composition disclosed herein may comprise one or more intact proteins. As used herein, the term "intact protein" refers to a protein in its original and undenatured condition. An "intact protein" can also be described as food protein or natural protein. Non-limiting sources of intact proteins may include meat, dairy, or plants. In various embodiments, a composition disclosed herein may comprise one or more intact proteins. In some aspects, an intact protein may be a high quality protein. As used herein, the term "high quality proteins" refers to a protein that includes all known EAAs and in a profile reasonably close to the profile of EAA requirements of a subject. In various embodiments, a composition disclosed herein may comprise one or more high quality proteins. In preferred embodiments, a composition disclosed herein may comprise whey protein.

In an aspect, inclusion of one or more intact proteins may amplify the stimulation of protein synthesis by prolonging the anabolic response because of slower digestion of EAAs compared the rate of digestion when consumed in free form and may provide sufficient NEAAs to support the maximal stimulation of protein synthesis. In some embodiments, a composition disclosed herein may comprise one or more intact proteins wherein the total amount of intact protein stimulates protein synthesis compared to a composition that does not contain intact proteins. In other embodiments, a composition disclosed herein may comprise one or more intact proteins wherein the total amount of intact protein stimulates protein synthesis by at least 2-fold compared to a composition that does not contain intact proteins. In other embodiments, a composition disclosed herein may comprise two or more EAAs and one or more intact proteins wherein the total amount of intact protein stimulates protein synthesis compared to a composition that consists of EAAs. In other embodiments, a composition disclosed herein may comprise two or more EAAs and one or more intact proteins wherein the total amount of intact protein stimulates protein synthesis by at least 2-fold compared to a composition that consists of free EAAs. In other embodiments a composition may comprise two, three, four, five, six, seven, or eight or more EAAs and one or more intact proteins.

In various embodiments, a composition may comprise about 30% to about 50% total intact dietary protein. In yet other embodiments, a composition may comprise about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, or about 50% total intact dietary protein.

(c) Nutrient Elements

In various embodiments, compositions disclosed herein may comprise one or more nutrient elements. As used herein, "nutrient elements" are substances that meet an essential nutritional need of a subject. Non limiting examples of nutrient elements comprise of vitamins, minerals, electrolytes, trace elements, and carbohydrates. Additionally, in various embodiments an amount of fat may be included with the composition.

In various embodiments, compositions disclosed herein may comprise one or more vitamins and similar compounds. Non-limiting examples of vitamins and similar compounds suitable for compositions disclosed herein may comprise vitamin A, vitamin D3, vitamin C, vitamin E, folic acid, thiamine, riboflavin, niacin, vitamin B6, vitamin B12, biotin, pantothenic acid, and vitamin K1. In some embodiments, compositions disclosed herein may comprise about 0.1% to about 10% total of one or more vitamins and similar compounds by weight of total weight of the composition.

In various embodiments, compositions disclosed herein may comprise one or more carbohydrates. In other embodiments, compositions disclosed herein may comprise one or more carbohydrates wherein the carbohydrates are selected from one or more simple saccharides. Non-limiting examples of simple saccharides include glucose, dextrose, fructose, corn syrup, and sucrose. In yet other embodiments, compositions disclosed herein may comprise one or more carbohydrates wherein the carbohydrates are selected from one or more complex saccharides. Non-limiting examples of complex saccharides include polyglucose and malto-dextrin. In still other embodiments, compositions disclosed herein may comprise a mixture of simple and complex saccharides. In an aspect, the ratio of simple saccharides to complex saccharides is about 75:25, about 50:50, or about 25:75. In some embodiments, compositions disclosed herein may comprise about 0.1% to about 10% total of one or more carbohydrates by weight of total weight of the composition.

In various embodiments, compositions disclosed herein may comprise at least one or more minerals and trace elements. Non-limiting examples of minerals and trace elements suitable for compositions disclosed herein may comprise iron, magnesium, copper, zinc, manganese, selenium, molybdenum, chromium, and iodide. In some embodiments, compositions disclosed herein may comprise about 0.1% to about 10% total of one or more minerals and/or trace elements by weight of total weight of the composition.

In various embodiments, compositions disclosed herein may comprise at least one or more electrolytes. Non-limiting examples of electrolytes suitable for compositions disclosed herein may comprise sodium, potassium, chloride, calcium, and phosphate. In preferred embodiments, compositions disclosed herein may comprise at least one or more electrolytes selected from the group comprising sodium and potassium.

In other embodiments, compositions disclosed herein may comprise about 0.25% to about 3% sodium by weight of total weight of the composition. In still other embodiments, compositions disclosed herein may comprise about 0.25%, about 0.50%, about 0.75%, about 1.0%, about 1.25%, about 1.50%, about 1.75%, about 2.0%, about 2.25%, about 2.50%, about 2.75%, or about 3.0% sodium by weight of total weight of the composition.

In other embodiments, compositions disclosed herein may comprise about 0.01% to about 1% potassium by weight of total weight of the composition. In still other embodiments, compositions disclosed herein may comprise about 0.01%, about 0.05%, about 0.10%, about 0.15%, about 0.2%, about 0.25%, about 0.3%, about 0.35%, about 0.4%, about 0.45%, about 0.5%, about 0.55%, about 0.6%, about 0.65%, about 0.7%, about 0.75%, about 0.8%, about 0.85%, about 0.9%, about 0.95%, or about 1% potassium by weight of total weight of the composition.

In still other embodiments, compositions disclosed herein may comprise about 0.25% to about 3% sodium by weight of total weight of the composition and about 0.01% to about 1% potassium by weight of total weight of the composition. In other embodiments, compositions may comprise about 0.55% to about 2% sodium by weight of total weight of the composition and about 0.1% to about 0.75% potassium by weight of total weight of the composition.

(d) Excipients

In various embodiments, compositions disclosed herein may comprise one or more excipients. As used herein, "excipients" refers to any substance that aids in formulating the composition to the desired form. Non-limiting examples of excipients include a buffering agent, a preservative, a stabilizer, a binder, a compaction agent, a lubricant, a dispersion enhancer, a disintegration agent, a flavoring agent, a sweetener, a coloring agent, and combinations of any of these agents.

In one embodiment, excipients comprising the composition may be one or more buffering agents. Non-limiting examples of suitable buffering agents include sodium citrate, magnesium carbonate, magnesium bicarbonate, calcium carbonate, and calcium bicarbonate.

In one embodiment, excipients comprising the composition may be one or more preservatives. Suitable examples of preservatives include, but are not limited to, antioxidants, such as alpha-tocopherol or ascorbate, and antimicrobials, such as parabens, chlorobutanol, phenol, or combinations thereof.

In another embodiment, excipients comprising the composition may be one or more binders. Suitable binders include, but are not limited to, starches, pregelatinized starches, gelatin, polyvinylpyrolidone, cellulose, methylcellulose, sodium carboxymethylcellulose, ethylcellulose, polyacrylamides, polyvinyloxoazolidone, polyvinylalcohols, C12-C18 fatty acid alcohol, polyethylene glycol, polyols, saccharides, oligosaccharides, polypeptides, oligopeptides, and combinations thereof.

In various embodiments, excipients comprising the composition may be one or more lubricants. Suitable non-limiting examples of lubricants include, but are not limited to, magnesium stearate, calcium stearate, zinc stearate, hydrogenated vegetable oils, sterotex, polyoxyethylene monostearate, talc, polyethyleneglycol, sodium benzoate, sodium lauryl sulfate, magnesium lauryl sulfate, light mineral oil.

In various embodiments, excipients comprising the composition may be one or more dispersion enhancers. Suitable dispersants may include, but are not limited to, starch, alginic acid, polyvinylpyrrolidones, guar gum, kaolin, bentonite, purified wood cellulose, sodium starch glycolate, isoamorphous silicate, and microcrystalline cellulose as high HLB emulsifier surfactants.

In yet another embodiment, excipients comprising the composition may be one or more disintegrants. In an aspect, a disintegrant may be a non-effervescent disintegrant. Suitable examples of non-effervescent disintegrants include, but are not limited to, starches such as corn starch, potato starch, pregelatinized and modified starches thereof, sweeteners, clays, such as bentonite, micro-crystalline cellulose, alginates, sodium starch glycolate, gums such as agar, guar, locust bean, karaya, pectin, and tragacanth. In another aspect, a disintegrant may be an effervescent disintegrant. Suitable effervescent disintegrants include, but are not limited to, sodium bicarbonate in combination with citric acid, and sodium bicarbonate in combination with tartaric acid.

In various embodiments, excipients comprising the composition may include one or more flavoring agents. In various embodiments, flavoring agent(s) may include synthetic flavor oils and flavoring aromatics and/or natural oils, extracts from plants, leaves, flowers, fruits, combinations thereof, or any other flavor recognized by those knowledgeable in the art. By way of non-limiting examples, these may include cinnamon oils, oil of wintergreen, peppermint oils, clover oil, hay oil, anise oil, eucalyptus, vanilla, citrus oil, such as lemon oil, orange oil, grape and grapefruit oil, and fruit essences including apple, peach, pear, strawberry, raspberry, cherry, plum, pineapple, and apricot.

In another embodiment, excipients comprising the composition may include a sweetener. By way of non-limiting example, the sweetener may be selected from glucose (corn syrup), dextrose, invert sugar, fructose, and mixtures thereof (when not used as a carrier); saccharin and its various salts such as the sodium salt; dipeptide sweeteners such as aspartame; dihydrochalcone compounds, glycyrrhizin; *Stevia rebaudiana* (Stevioside); chloro derivatives of sucrose such as sucralose; and sugar alcohols such as sorbitol, mannitol, sylitol, and the like. Also contemplated are hydrogenated starch hydrolysates and the synthetic sweetener 3,6-dihydro-6-methyl-1,2,3-oxathiazin-4-one-2,2-dioxide, particularly the potassium salt (acesulfame-K), and sodium and calcium salts thereof.

In another embodiment, excipients comprising the composition may include actives, emulsifying agents, suspending agents, diluents, sweeteners, coloring agents, and flavoring agents. Depending upon the embodiment, it may be desirable to provide a coloring agent in the outer layer in addition to or instead of flavoring. Suitable color additives include food, drug and cosmetic colors (FD&C), drug and cosmetic colors (D&C), or external drug and cosmetic colors (Ext. D&C). These colors or dyes, along with their corresponding lakes, and certain natural and derived colorants may be suitable for use in the compositions described herein depending on the embodiment.

(e) Dosage Forms

In various embodiments, compositions disclosed herein may be an oral dosage form. As used herein, the term "oral dosage form" refers to a dosage form that comprises pharmaceutically acceptable ingredients and is to be administered orally to a subject. An oral dosage form may be classified, for example, as a dietary supplement, a drug, and/or a biologic material depending on the contents of the oral dosage form, its intended use, and the country in which it is sold. A dosage form may be intended to treat or prevent a condition or disease, or the symptoms associated therewith. A dosage form may also be a means of addressing a lack of availability of a critical material in an individual's diet. It is not a requirement that a dosage form is classified as a drug. A dosage form may, for example but not limited to, be a dietary supplement if it is intended to treat or prevent a condition.

In various embodiments, compositions disclosed herein may be a liquid dosage form. Non-limiting examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules.

In various embodiments, compositions disclosed herein may be a solid dosage form. In other embodiments, a solid dosage form of a composition disclosed herein may be an oral dosage form. In yet other embodiments, a solid dosage form of a composition disclosed herein may be a tablet, a capsule, a granule or a powder. In still other embodiments, a solid dosage composition may be incorporated into a food product. In other embodiments, a solid dosage composition may be incorporated into a food product. In an aspect, a food product for use herein may be a drink. Non-limiting examples of a suitable drink include fruit juice, a fruit drink, an artificially flavored drink, an artificially sweetened drink, a carbonated beverage, a sports drink, and so forth. In another aspect, the food product may also be a solid foodstuff. Suitable examples of a solid foodstuff include a food bar, a snack bar, a cookie, a brownie, a muffin, a cracker, and the like.

(II) Uses of Compositions

In various embodiments, the compositions disclosed herein may comprise a formulation effective for increasing protein synthesis, for promoting muscle anabolism, for preserving muscle mass and strength, or for prevention of muscle atrophy, administration to a subject in need thereof.

A suitable subject includes a human, a livestock animal, a companion animal, a lab animal, or a zoological animal. In one embodiment, the subject may be a rodent, e.g., a mouse, a rat, a guinea pig, etc. In another embodiment, the subject may be a livestock animal. Non-limiting examples of suitable livestock animals may include pigs, cows, horses, goats, sheep, llamas and alpacas. In yet another embodiment, the subject may be a companion animal. Non-limiting examples of companion animals may include pets such as dogs, cats, rabbits, and birds. In yet another embodiment, the subject may be a zoological animal. As used herein, a "zoological animal" refers to an animal that may be found in a zoo. Such animals may include non-human primates, large cats, wolves, and bears. In a specific embodiment, the animal is a laboratory animal. Non-limiting examples of a laboratory animal may include rodents, canines, felines, and non-human primates. In certain embodiments, the animal is a rodent. Non-limiting examples of rodents may include mice, rats, guinea pigs, etc. In preferred embodiments, the subject is a human.

In some embodiments, the subject may be young, middle-aged, or elderly. As used herein, "young" refers to a human subject that is up to about 40 years of age. As used herein, "middle-aged" refers to a human subject that is about 40 years of age to about 65 years of age. As used herein, "elderly" refers to a human subject that is at least about 65 years of age. In some embodiments, the subject may be underweight, normal weight, overweight, or obese. As used herein "underweight" can refer to a subject with a Body Mass Index (BMI) up to about 18.5. As used herein "normal weight" can refer to a subject with a BMI of about 18.5 to about 25. As used herein "overweight" can refer to a subject with a BMI of about 25 to about 30. As used herein "obese" can refer to a subject with a BMI no less than about 30. In other embodiments, the subject may be healthy. In some embodiments, the subject may be recovering from injury. In still other embodiments, the subject may be recovering from stress. In an aspect, a subject is recovering from surgery-induced stress. In another aspect, a subject is recovering from exercise. In yet other embodiments, the subject may have a condition. Non-limiting examples of conditions as used herein include cardiovascular disease, hypertension, osteoporosis, diabetes, metabolic disorder, cancer, and the like.

(a) Increasing Protein Synthesis

In various embodiments, compositions disclosed herein may comprise a formulation effective for increasing protein synthesis, including protein synthesis. As used herein, "protein synthesis" refers to the molecular mechanisms within the muscle cell responsible for the creation of new proteins in the body. In some embodiments, compositions disclosed herein may comprise a formulation effective for increasing protein synthesis at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% following administration to a subject. In other aspects, an increase protein synthesis following administration of a composition disclosed herein may occur in a dose dependent manner.

In some embodiments, compositions disclosed herein may comprise a formulation effective for increasing protein synthesis at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% following administration to a young subject. In other embodiments, compositions disclosed herein may comprise a formulation effective for increasing protein synthesis at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% following administration to a middle-aged subject. In still other embodiments, compositions disclosed herein may comprise a formulation effective for increasing protein synthesis at least 5%, at least 10%, at least 15%, at least 20%, at least 25%, at least 30%, at least 35%, at least 40%, at least 45%, or at least 50% following administration to an elderly subject.

In some embodiments, compositions disclosed herein may comprise a formulation effective for increasing protein synthesis at least 5%, at least 10%, at least 15%, at least 20%, at least 25%, at least 30%, at least 35%, at least 40%, at least 45%, or at least 50% following administration to a underweight subject. In other embodiments, compositions disclosed herein may comprise a formulation effective for increasing protein synthesis at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% following administration to a subject of normal weight. In some embodiments, compositions disclosed herein may comprise a formulation effective for increasing protein synthesis at least 5%, at least 10%, at least 15%, at least 20%, at least 25%, at least 30%, at least 35%, at least 40%, at least 45%, or at least 50% following administration to an overweight subject. In still other embodiments, compositions disclosed herein may comprise a formulation effective for increasing protein synthesis at least 5%, at least 10%, at least 15%, at least 20%, at least 25%, at least 30%, at least 35%, at least 40%, at least 45%, or at least 50% following administration to an obese subject.

In some embodiments, compositions disclosed herein may comprise a formulation effective for increasing protein synthesis at least 5%, at least 10%, at least 15%, at least 20%, at least 25%, at least 30%, at least 35%, at least 40%, at least 45%, or at least 50% following administration to a subject with a condition wherein the condition may be cardiovascular disease, hypertension, osteoporosis, diabetes, metabolic disorder, or cancer.

In some embodiments, compositions disclosed herein may comprise a formulation effective for increasing protein synthesis at least 5%, at least 10%, at least 15%, at least 20%, at least 25%, at least 30%, at least 35%, at least 40%, at least 45%, or at least 50% following administration to a stressed subject. In other aspects, compositions disclosed herein may comprise a formulation effective for increasing protein synthesis in subjects with injury-induced stress. In still other aspects, compositions disclosed herein may comprise a formulation effective for increasing protein synthesis in subjects with inactivity-induced stress. In other aspects, compositions disclosed herein may comprise a formulation effective for increasing protein synthesis in subjects with immobility-induced stress.

In still other aspects, compositions disclosed herein may comprise a formulation effective for increasing protein synthesis in subjects with exercise-induced stress. In other embodiments, compositions may comprise a formulation effective for increasing protein synthesis following administration of the composition to a subject following an exercise regimen wherein the formulation increases protein synthesis at least 5%, at least 10%, at least 15%, at least 20%, at least 25%, at least 30%, at least 35%, at least 40%, at least 45%, or at least 50% compared to exercise alone.

In additional embodiments, compositions disclosed herein may comprise a formulation effective for increasing protein synthesis in subjects with surgery-induced stress. In some aspects, compositions disclosed herein may comprise a formulation effective for increasing protein synthesis in subjects with surgery-induced stress wherein the composition is administered about 30 minutes, about 1 hour, about 6 hours, about 12 hours, about 24 hours, about 2 days, about 3 days, about 4 days, about 5 days, about 6 days, about 1 week, about 2 weeks, about 1 month, about 6 months, or about 1 year after surgery or injury. In other embodiments, compositions disclosed herein may comprise a formulation effective for increases protein synthesis at least 5%, at least 10%, at least 15%, at least 20%, at least 25%, at least 30%, at least 35%, at least 40%, at least 45%, or at least 50% after surgery compared to subjects not administered a composition.

(b) Promoting Anabolism

In some embodiments, compositions disclosed herein may comprise a formulation effective for promoting anabolism, or gain of body protein, including muscle protein. As used herein, "anabolism" includes an increase in muscle mass and/or muscle strength. In some embodiments, compositions disclosed herein may comprise a formulation effective for promoting muscle anabolism at least 10%, at least 20%, at least 30%, at least 40% or at least 50% or more following administration to a subject. In other aspects, an increase in muscle anabolism following administration of a composition disclosed herein may occur in a dose dependent manner. [Please confirm].

In some embodiments, compositions disclosed herein may comprise a formulation effective for promoting anabolism at least 10%, at least 20%, at least 30%, at least 40% or at least 50% or more following administration to a young subject. In other embodiments, compositions disclosed herein may comprise a formulation effective for promoting at least 10%, at least 20%, at least 30%, at least 40% or at least 50% or more following administration to a middle-aged subject. In still other embodiments, compositions disclosed herein may comprise a formulation effective for promoting at least 10%, at least 20%, at least 30%, at least 40% or at least 50% or more following administration to an elderly subject.

In some embodiments, compositions disclosed herein may comprise a formulation effective for promoting at least 10%, at least 20%, at least 30%, at least 40% or at least 50% or more following administration to an underweight subject. In other embodiments, compositions disclosed herein may comprise a formulation effective for promoting anabolism at least 10%, at least 20%, at least 30%, at least 40% or at least 50% or more following administration to a subject of normal weight. In some embodiments, compositions disclosed herein may comprise a formulation effective for promoting anabolism at least 10%, at least 20%, at least 30%, at least 40% or at least 50% or more following administration to an overweight subject. In still other embodiments, compositions disclosed herein may comprise a formulation effective for promoting at least 10% at least 20%, at least 30%, at least 40% or at least 50% or more following administration to an obese subject.

In some embodiments, compositions disclosed herein may comprise a formulation effective for promoting anabolism at least 10%, at least 20%, at least 30%, at least 40% or at least 50% or more following administration to a subject with a condition wherein the condition may be cardiovascular disease, hypertension, osteoporosis, diabetes, metabolic disorder, or cancer.

In some embodiments, compositions disclosed herein may comprise a formulation effective for promoting at least 10%, at least 20%, at least 30%, at least 40% or at least 50% or more following administration to a stressed subject. In other aspects, compositions disclosed herein may comprise a formulation effective for promoting anabolism in subjects with injury-induced stress. In still other aspects, compositions disclosed herein may comprise a formulation effective for promoting anabolism in subjects with inactivity-induced stress. In other aspects, compositions disclosed herein may comprise a formulation effective for promoting muscle anabolism in subjects with immobility-induced stress.

In still other aspects, compositions disclosed herein may comprise a formulation effective for promoting anabolism in subjects wherein the formulation is administered following an exercise regimen. In other embodiments, compositions may comprise a formulation effective for promoting anabolism when administered to a subject following an exercise regimen wherein the formulation promotes muscle anabolism at least 100%, at least 200%, at least 300%, at least 400% or at least 500% compared to exercise alone.

In additional embodiments, compositions disclosed herein may comprise a formulation effective for promoting anabolism in subjects with surgery-induced stress. In some aspects, compositions disclosed herein may comprise a formulation effective for promoting anabolism in subjects with surgery-induced stress wherein the composition is administered about 30 minutes, about 1 hour, about 6 hours, about 12 hours, about 24 hours, about 2 days, about 3 days, about 4 days, about 5 days, about 6 days, about 1 week, about 2 weeks, about 1 month, about 6 months, or about 1 year after surgery. In other embodiments, compositions disclosed herein may comprise a formulation effective for promoting net anabolism at least 5%, at least 10%, at least 15%, at least 20%, at least 25%, at least 30%, at least 35%, at least 40%, at least 45%, or at least 50%, at least 55%, at least 60%, at least 65%, at least 70%, at least 75%, at least 80%, at least 95%, or at least 100% in a subject following surgery compared to subjects not administered a composition.

(c) Preserving Muscle Mass and Strength

In some embodiments, compositions disclosed herein may comprise a formulation effective for preserving muscle mass and/or strength. As used herein, "preserving muscle mass and strength" refers to preservation of muscle mass and/or muscle strength in subjects under circumstances in which muscle loss may occur. Non-limiting examples of circumstances that may result in muscle loss of a subject include increased age, increased weight, immobility over time, periods of inactivity, surgery, injury, and disease. In some embodiments, compositions disclosed herein may comprise a formulation effective for preserving muscle mass and/or strength at least 5%, at least 10%, at least 15%, at least 20%, at least 25%, at least 30%, at least 35%, at least 40%, at least 45%, or at least 50% following administration to a subject. In other aspects, preservation of muscle mass and/or strength following administration of a composition disclosed herein may occur in a dose dependent manner.

In some embodiments, compositions disclosed herein may comprise a formulation effective for preserving muscle mass and/or strength at least 5%, at least 10%, at least 15%, at least 20%, at least 25%, at least 30%, at least 35%, at least 40%, at least 45%, or at least 50% following administration to a young subject. In other embodiments, compositions disclosed herein may comprise a formulation effective for preserving muscle mass and/or strength at least 5%, at least 10%, at least 15%, at least 20%, at least 25%, at least 30%, at least 35%, at least 40%, at least 45%, or at least 50% following administration to a middle-aged subject. In still other embodiments, compositions disclosed herein may comprise a formulation effective for preserving muscle mass and/or strength at least 5%, at least 10%, at least 15%, at least 20%, at least 25%, at least 30%, at least 35%, at least 40%, at least 45%, or at least 50% following administration to an elderly subject.

In some embodiments, compositions disclosed herein may comprise a formulation effective for preserving muscle mass and/or strength at least 5%, at least 10%, at least 15%, at least 20%, at least 25%, at least 30%, at least 35%, at least 40%, at least 45%, or at least 50% following administration to an underweight subject. In other embodiments, compositions disclosed herein may comprise a formulation effective for preserving muscle mass and/or strength at least 5%, at least 10%, at least 15%, at least 20%, at least 25%, at least 30%, at least 35%, at least 40%, at least 45%, or at least 50% following administration to a subject of normal weight. In some embodiments, compositions disclosed herein may comprise a formulation effective for preserving muscle mass and/or strength at least 5%, at least 10%, at least 15%, at least 20%, at least 25%, at least 30%, at least 35%, at least 40%, at least 45%, or at least 50% following administration to an overweight subject. In still other embodiments, compositions disclosed herein may comprise a formulation effective for preserving muscle mass and/or strength at least 5%, at least 10%, at least 15%, at least 20%, at least 25%, at least 30%, at least 35%, at least 40%, at least 45%, or at least 50% following administration to an obese subject.

In some embodiments, compositions disclosed herein may comprise a formulation effective for preserving muscle mass and/or strength at least 5%, at least 10%, at least 15%, at least 20%, at least 25%, at least 30%, at least 35%, at least 40%, at least 45%, or at least 50% following administration to a subject with a condition wherein the condition may be cardiovascular disease, hypertension, osteoporosis, diabetes, metabolic disorder, or cancer.

In some embodiments, compositions disclosed herein may comprise a formulation effective for preserving muscle mass and/or strength at least 5%, at least 10%, at least 15%, at least 20%, at least 25%, at least 30%, at least 35%, at least 40%, at least 45%, at least 50%, at least 55%, at least 60%, at least 65%, or at least 70% following administration to a stressed subject. In other aspects, compositions disclosed herein may comprise a formulation effective for preserving muscle mass and/or strength in subjects with injury-induced stress. In still other aspects, compositions disclosed herein may comprise a formulation effective for preserving muscle mass and/or strength in subjects with inactivity-induced stress. In other aspects, compositions disclosed herein may comprise a formulation effective for preserving muscle mass and/or strength in subjects with immobility-induced stress.

In additional embodiments, compositions disclosed herein may comprise a formulation effective for preserving muscle mass and/or strength in subjects with surgery-induced stress. In some aspects, compositions disclosed herein may comprise a formulation effective for preserving muscle mass and/or strength in subjects with surgery-induced stress wherein the composition is administered about 30 minutes, about 1 hour, about 6 hours, about 12 hours, about 24 hours, about 2 days, about 3 days, about 4 days, about 5 days, about 6 days, about 1 week, about 2 weeks, about 1 month, about 6 months, or about 1 year after surgery. In other embodiments, compositions disclosed herein may comprise a formulation effective for preserving muscle mass and/or strength at least 5%, at least 10%, at least 15%, at least 20%, at least 25%, at least 30%, at least 35%, at least 40%, at least 45%, at least 50%, at least 55%, at least 60%, at least 65%, or at least 70% when administered after surgery compared to subjects not administered a composition (d) Prevention of Muscle Atrophy In some embodiments, compositions disclosed herein may comprise a formulation effective for prevention of muscle atrophy. As used herein, "prevention of muscle atrophy" refers to preventing loss of muscle mass and/or muscle strength in subjects who are at risk of muscle atrophy. Non-limiting examples of risk factors that may lead to muscle atrophy in a subject include increased age, increased weight, immobility over time, periods of inactivity, surgery, injury, and disease. In some embodiments, compositions disclosed herein may comprise a formulation effective for preventing muscle atrophy at least 5%, at least 10%, at least 15%, at least 20%, at least 25%, at least 30%, at least 35%, at least 40%, at least 45%, at least 50%, at least 55%, at least 60%, at least 65%, or at least 70% following administration to a subject. In other aspects, preventing muscle atrophy following administration of a composition disclosed herein occurs in a dose dependent manner.

In some embodiments, compositions disclosed herein may comprise a formulation effective for preventing muscle atrophy by at least 5%, at least 10%, at least 15%, at least 20%, at least 25%, at least 30%, at least 35%, at least 40%, at least 45%, at least 50%, at least 55%, at least 60%, at least 65%, or at least 70% following administration to a young subject. In other embodiments, compositions disclosed herein may comprise a formulation effective for preventing muscle atrophy by at least 5%, at least 10%, at least 15%, at least 20%, at least 25%, at least 30%, at least 35%, at least 40%, at least 45%, at least 50%, at least 55%, at least 60%, at least 65%, or at least 70% following administration to a middle-aged subject. In still other embodiments, compositions disclosed herein may comprise a formulation effective for preventing muscle atrophy by at least 5%, at least 10%, at least 15%, at least 20%, at least 25%, at least 30%, at least 35%, at least 40%, at least 45%, at least 50%, at least 55%, at least 60%, at least 65%, or at least 70% following administration to an elderly subject.

In some embodiments, compositions disclosed herein may comprise a formulation effective for preventing muscle atrophy by at least 5%, at least 10%, at least 15%, at least 20%, at least 25%, at least 30%, at least 35%, at least 40%, at least 45%, at least 50%, at least 55%, at least 60%, at least 65%, or at least 70% following administration to a underweight subject. In other embodiments, compositions disclosed herein may comprise a formulation effective for preventing muscle atrophy by at least 5%, at least 10%, at least 15%, at least 20%, at least 25%, at least 30%, at least 35%, at least 40%, at least 45%, at least 50%, at least 55%, at least 60%, at least 65%, or at least 70% following administration to a subject of normal weight. In some embodiments, compositions disclosed herein may comprise a formulation effective for preventing muscle atrophy by at least 5%, at least 10%, at least 15%, at least 20%, at least 25%, at least 30%, at least 35%, at least 40%, at least 45%, at least 50%, at least 55%, at least 60%, at least 65%, or at least 70% following administration to an overweight subject. In still other embodiments, compositions disclosed herein may comprise a formulation effective for preventing muscle atrophy by at least 5%, at least 10%, at least 15%, at least 20%, at least 25%, at least 30%, at least 35%, at least 40%, at least 45%, at least 50%, at least 55%, at least 60%, at least 65%, or at least 70% following administration to an obese subject.

In some embodiments, compositions disclosed herein may comprise a formulation effective for preventing muscle atrophy by at least 5%, at least 10%, at least 15%, at least 20%, at least 25%, at least 30%, at least 35%, at least 40%, at least 45%, at least 50%, at least 55%, at least 60%, at least 65%, or at least 70% following administration to a subject with a condition wherein the condition may be cardiovascular disease, hypertension, osteoporosis, diabetes, metabolic disorder, or cancer.

In some embodiments, compositions disclosed herein may comprise a formulation effective for preventing muscle atrophy by least 5%, at least 10%, at least 15%, at least 20%, at least 25%, at least 30%, at least 35%, at least 40%, at least 45%, at least 50%, at least 55%, at least 60%, at least 65%, or at least 70% following administration to a stressed subject. In other aspects, compositions disclosed herein may comprise a formulation effective for preventing muscle atrophy in subjects with injury-induced stress. In still other aspects, compositions disclosed herein may comprise a formulation effective for preventing muscle atrophy in subjects with inactivity-induced stress. In other aspects, compositions disclosed herein may comprise a formulation effective preventing muscle atrophy in subjects with immobility-induced stress.

In additional embodiments, compositions disclosed herein may comprise a formulation effective for preventing muscle atrophy in subjects with surgery-induced stress. In some aspects, compositions disclosed herein may comprise a formulation effective for preventing muscle atrophy in subjects with surgery-induced stress wherein the composition is administered about 30 minutes, about 1 hour, about 6 hours, about 12 hours, about 24 hours, about 2 days, about 3 days, about 4 days, about 5 days, about 6 days, about 1 week, about 2 weeks, about 1 month, about 6 months, or about 1 year after surgery. In other embodiments, compositions disclosed herein may comprise a formulation effective for preventing muscle atrophy at least 5%, at least 10%, at least 15%, at least 20%, at least 25%, at least 30%, at least 35%, at least 40%, at least 45%, or at least 50% when administered after surgery compared to subjects not administered a composition.

(III) Kits and Packaging of Compositions

In various embodiments, the present disclosure provides a kit comprising at least one or more compositions disclosed herein. In other embodiments, the present disclosure provides packaging comprising at least one or more compositions disclosed herein.

(a) Kits

The present disclosure may further comprise a kit, wherein the kit comprises at least a composition as described herein. In various embodiments, a kit may further comprise one or more additional compositions, instructions for applying the composition(s), instructions for complying with a suitable application regimen, an implement, a substrate, a delivery enhancement device, a dietary supplement, or combinations thereof. In some aspects, a kit may comprise an outer packaging unit, which in turn may comprise one or more smaller, inner packaging units. In further aspects, inner packaging units may comprise one or more of individual components of the kit. In other aspects, inner and outer packaging units may be of any type suitable for containing, presenting and/or reasonably protecting from damage the contents of the kit. In still other aspects, inner packaging units may contain a quantity of a composition suitable for at least one dose, at least two doses, at least three doses, at least four doses, at least 5 doses, at least 6 doses, at least 7 doses, at least 8 doses, at least 9 doses, at least 10 doses, at least 11 doses, or at least 12 doses. In additional aspects, a kit may comprise one or more containers wherein the containers may be filled with one or more of the ingredients of a composition disclosed herein. In a non-limiting example, the kit can comprise a powdered drink mix and a composition disclosed herein.

In various embodiments, a kit may further comprise instructions for methods of use. In some aspects, instructions to be provided with a kit may be in a fixed form. Non-limiting examples of fixed form instructions include written, recorded onto an audiocassette, videocassette, compact disc, or digital videodisc. In other aspects, a kit may comprise a notice in the form prescribed by a government agency regulating the manufacture, use or sale of pharmaceutical products, which notice reflects approval by the agency of manufacture, use of sale for human administration. In still other aspects, a kit may be labeled with information regarding mode of administration, sequence of administration, or the like. In other aspects, a kit may include means for reminding the subject to administer a composition. In other embodiments, a kit may further comprise a virtual package. As used herein, a "virtual package" refers to components of a kit that are associated by directions on one or more physical or virtual kit components instructing the user how to obtain the other components. A non-limiting example of a virtual package includes a bag or other container containing one component and directions instructing a subject to go to a website, contact a recorded message or a fax-back service, view a visual message, or contact a caregiver or instructor to obtain instructions on how to use the kit or safety or technical information about one or more components of a kit.

In other embodiments, a kit may be a single package. As used herein, the term "single package" means that the components of a kit are physically associated in or with one or more containers and considered a unit for manufacture, distribution, sale, or use. Examples of containers include, but are not limited to, bags, boxes, cartons, bottles, packages such as shrink-wrap packages, stapled or otherwise affixed components, or combinations thereof. In some aspects, a single package may comprise containers of compositions disclosed herein and food products physically associated such that they are considered a unit for manufacture, distribution, sale, or use.

In some embodiments, a kit may comprise one or more components to assist administration of a composition described herein. Non-limiting examples of such components include syringes, measuring spoons or cups, spoons, and straws. In other embodiments, a kit may comprise a composition as disclosed herein and a food product wherein the composition may be incorporated into a food product. In an aspect, a food product for use herein may be a drink. Non-limiting examples of a suitable drink include fruit juice, a fruit drink, an artificially flavored drink, an artificially sweetened drink, a carbonated beverage, a sports drink, and so forth. In another aspect, the food product may also be a solid foodstuff. Suitable examples of a solid foodstuff include a food bar, a snack bar, a cookie, a brownie, a muffin, a cracker, and the like.

(b) Packaging

In various embodiments, compositions disclosed herein may be packaged. In some aspects, packaging of a composition may be for storage, shipment, display for sale, or a combination thereof. In various aspects, compositions may be packaged using one or more suitable materials known in the art. In other aspects, compositions may be packaged using one or more suitable methods known in the art. In some aspects, the choice of packaging material and/or packaging method is dependent on the dosage form of a composition disclosed herein to be packaged.

In some embodiments, compositions disclosed herein may be packaged wherein packaging increases the length of time a composition can be stored. As used herein, the "shelf-life" of a composition is the length of time after formulation that a composition can maintain one or more physiological effects following administration to a subject as detailed herein. In some aspects, compositions disclosed herein may be packaged wherein packaging increases the shelf-life of a composition by about 1 week, about 1 month, about 6 month, about 1 year, about 2 years, about 3 years, or about 4 years after formulation. In other embodiments, compositions disclosed herein may be packaged wherein packaging increases the length of time a composition can be stored at room temperature. As used herein, room temperature may be about 20° C. to about 25° C. In some aspects, compositions disclosed herein may be packaged wherein packaging increases the length of time a composition can be stored at room temperature by about 1 week, about 1 month, about 6 month, about 1 year, about 2 years, about 3 years, or about 4 years.

In other embodiments, compositions disclosed herein may be packaged wherein the packaging allows for the packaged composition to be frozen. In some aspects, the packaging allows for the packaged composition to be frozen for about 1 week, about 1 month, about 6 month, about 1 year, about 2 years, about 3 years, or about 4 years. In still other embodiments, compositions disclosed herein may be packaged wherein the packaging allows for the packaged composition to be heated. In some aspects, the packaging allows for the packaged composition to be cooked.

(IV) Methods of Using Compositions

Other aspects of the present invention are methods of administering a composition disclosed herein to a subject wherein administration increases protein synthesis, promotes anabolism, preserves or improves muscle mass and strength and prevents muscle atrophy.

(a) Methods of Administration

In various embodiments, methods of administration of a composition may include administration of a liquid composition to increase protein synthesis in a subject. In various embodiments, compositions disclosed herein may be a liquid dosage form. Non-limiting examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. In other embodiments, administration of a composition may include a solid dosage form to increase protein synthesis in a subject. In yet other embodiments, methods of administration of a composition may include administration of a solid dosage form of a composition disclosed herein may be a tablet, a capsule, a granule or a powder. In still other embodiments, a solid dosage composition may be incorporated into a food product. In other embodiments, a solid dosage composition may be incorporated into a food product. In an aspect, a food product for use herein may be a drink. Non-limiting examples of a suitable drink include fruit juice, a fruit drink, an artificially flavored drink, an artificially sweetened drink, a carbonated beverage, a sports drink, and so forth. In another aspect, the food product may also be a solid foodstuff. Suitable examples of a solid foodstuff include a food bar, a snack bar, a cookie, a brownie, a muffin, a cracker, and the like.

In various embodiments, administration of a composition disclosed herein may be administered to a subject about once a day, about twice a day, about three times a day. In other embodiments, administration of a composition disclosed herein may be administered to a subject at least once a day, at least once a day for about 2 days, at least once a day for about 3 days, at least once a day for about 4 days, at least once a day for about 5 days, at least once a day for about 6 days, at least once a day for about 1 week, at least once a day for about 2 weeks, at least once a day for about 3 weeks, at least once a day for about 4 weeks, at least once a day for about 8 weeks, at least once a day for about 12 weeks, at least once a day for about 16 weeks, at least once a day for about 24 weeks, at least once a day for about 52 weeks and thereafter. In other embodiments, administration of a composition disclosed herein may be administered to a subject at least once every other day, at least once every other day for about 2 days, at least once every other day for about 3 days, at least once every other day for about 4 days, at least once every other day for about 5 days, at least once every other day for about 6 days, at least once every other day for about 1 week, at least once every other day for about 2 weeks, at least once every other day for about 3 weeks, at least once every other day for about 4 weeks, at least once every other day for about 8 weeks, at least once every other day for about 12 weeks, at least once every other day for about 16 weeks, at least once every other day for about 24 weeks, at least once every other day for about 52 weeks and thereafter. In still other embodiments, administration of a composition disclosed herein may be administered to a subject at least once every 3 days, at least once every 3 days for about 6 days, at least once every 3 days for about 1 week, at least once every 3 days for about 2 weeks, at least once every 3 days for about 3 weeks, at least once every 3 days for about 4 weeks, at least once every 3 days for about 8 weeks, at least once every 3 days for about 12 weeks, at least once every 3 days for about 16 weeks, at least once every 3 days for about 24 weeks, at least once every 3 days for 52 weeks and thereafter. In other embodiments, administration of a composition disclosed herein may be administered to a subject at least once a week, at least once a week for about 2 weeks, at least once a week for about 3 weeks, at least once a week for about 4 weeks, at least once a week for about 8 weeks, at least once a week for about 12 weeks, at least once a week for about 16 weeks, at least once a week for about 24 weeks, at least once a week for about 52 weeks and thereafter.

(b) Methods of Increasing Protein Synthesis

In various embodiments, a method of increasing protein synthesis may include administration of a composition disclosed herein. In preferred embodiments, a method of increasing protein synthesis may include oral administration of a composition disclosed herein.

In some aspects, administration of at least about 1 gram to about 11 grams of a composition disclosed herein may increase protein synthesis in a subject. In various embodiments, administration of a composition disclosed herein comprising one or more EAAs may increase protein synthesis in a subject. In other aspects, administration of a composition disclosed herein comprising at least about 1 gram to about 11 grams of total EEAs may increase protein synthesis in a subject. In still other aspects, administration of a composition disclosed herein comprising at least 1 gram, at least 2 grams, at least 3 grams, at least 4 grams, at least 5 grams, at least 6 grams, at least 7 grams, at least 8 grams, at least 9 grams, at least 10 grams, or at least 11 grams of total EEAs may increase protein synthesis in a subject.

In various embodiments, administration of a composition disclosed herein comprising one or more NEAAs may increase protein synthesis in a subject. In some aspects, administration of a composition disclosed herein comprising about 0.5 grams to about 2.5 grams total NEAAs may increase protein synthesis in a subject. In still other aspects, administration of a composition disclosed herein comprising at least about 0.5 grams, about 0.6 grams, about 0.7 grams, about 0.8 grams, about 0.9 grams, about 1.0 grams, about 1.1 grams, about 1.2 grams, about 1.3 grams, about 1.4 grams, about 1.5 grams, about 1.6 grams, about 1.7 grams, about 1.8 grams, about 1.9 grams, about 2.0 grams, about 2.1 grams, about 2.2 grams, about 2.3 grams, about 2.4 grams, about 2.5 grams, about 2.6 grams, about 2.7 grams, about 2.8 grams, about 2.9 grams, about 3.0 grams, about 3.1 grams, about 3.2 grams, about 3.3 grams, about 3.4 grams, about 3.5 grams, about 3.6 grams, about 3.7 grams, about 3.8 grams, about 3.9 grams, or about 4.0 grams total NEAAs may increase protein synthesis in a subject.

In various embodiments, administration of a composition disclosed herein comprising about 15% NEAAs and about 85% EAAs, about 16% NEAAs and about 84% EAAs, about 17% NEAAs and about 83% EAAs, about 18% NEAAs and about 82% EAAs, about 19% NEAAs and about 81% EAAs, or about 20% NEAAs and about 85% EAAs by weight of total weight of the composition including NEAAs from the protein may increase protein synthesis in a subject.

In some embodiments, administration of a composition disclosed herein comprising creatine increases protein synthesis. In other embodiments, administration of a composition disclosed herein comprising about 5% to about 10% creatine may increase protein synthesis in a subject. In some embodiments, administration of a composition disclosed herein comprising creatine and EAAs increases protein synthesis compared to administration of a composition consisting of only EAAs. In various embodiments, administration of a composition disclosed herein comprising creatine and EAAs increases protein synthesis by at least 25% compared to administration of a composition consisting of only EAAs.

In some embodiments, administration of a composition comprising one or more intact proteins may increase protein synthesis in a subject. In some aspects, the intact protein may be whey protein. In other embodiments, administration of a composition disclosed herein comprising about 30% to about 50% total intact dietary protein may increase protein synthesis in a subject. In some embodiments, administration of a composition disclosed herein comprising intact protein and one or more EAAs increases protein synthesis compared to administration of a composition consisting of EAAs. In various embodiments, administration of a composition disclosed herein comprising intact protein and one or more EAAs increases protein synthesis by at least 2-fold compared to administration of a composition consisting of only EAAs.

In various embodiments, administration of a composition comprising one or more nutrient elements may increase protein synthesis in a subject. In other embodiments, administration of a composition comprising about 8% to about 12% citrulline may increase protein synthesis in a subject.

In some embodiments, administration of a composition disclosed herein may increase protein synthesis in a subject by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% following administration to a subject. In some embodiments, administration of a composition disclosed herein may increase protein synthesis in a subject by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% compared to exercise alone. In other embodiments, administration of a composition disclosed herein may increase protein synthesis in a subject by in a dose dependent manner.

In some embodiments, administration of a composition disclosed herein may increase protein synthesis in a subject by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% following administration to a young subject. In other embodiments, administration of a composition disclosed herein may increase protein synthesis in a subject by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% following administration to a middle-aged subject. In some embodiments, administration of a composition disclosed herein may increase protein synthesis in a subject by at least 5%, at least 10%, at least 15%, at least 20%, at least 25%, at least 30%, at least 35%, at least 40%, at least 45%, or at least 50% following administration to an elderly subject.

In some embodiments, administration of a composition disclosed herein may increase protein synthesis in a subject by at least 5%, at least 10%, at least 15%, at least 20%, at least 25%, at least 30%, at least 35%, at least 40%, at least 45%, or at least 50% following administration to a underweight subject. In other embodiments, administration of a composition disclosed herein may increase protein synthesis in a subject by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% following administration to a subject of normal weight. In still other embodiments, administration of a composition disclosed herein may increase protein synthesis in a subject by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% following administration to an overweight subject. In some embodiments, administration of a composition disclosed herein may increase protein synthesis in a subject by at least 5%, at least 10%, at least 15%, at least 20%, at least 25%, at least 30%, at least 35%, at least 40%, at least 45%, or at least 50% following administration to an obese subject.

In other embodiments, administration of a composition disclosed herein may increase protein synthesis in a subject by at least 5%, at least 10%, at least 15%, at least 20%, at least 25%, at least 30%, at least 35%, at least 40%, at least 45%, or at least 50% following administration to a subject with a condition wherein the condition may be cardiovascular disease, hypertension, osteoporosis, diabetes, metabolic disorder, or cancer.

In some embodiments, administration of a composition disclosed herein may increase protein synthesis in a subject by at least 5%, at least 10%, at least 15%, at least 20%, at least 25%, at least 30%, at least 35%, at least 40%, at least 45%, or at least 50% following administration to a stressed subject. In other aspects, administration of a composition disclosed herein may increase protein synthesis in subjects with injury-induced stress. In still other aspects, administration of a composition disclosed herein may increase protein synthesis in subjects with inactivity-induced stress. In other aspects, administration of a composition disclosed herein may increase protein synthesis in subjects with immobility-induced stress.

In still other aspects, administration of a composition disclosed herein may increase protein synthesis in subjects wherein the composition is administered following an exercise regimen. In other embodiments, administration of a composition disclosed herein to a subject following an exercise regimen may increase protein synthesis at least 5%, at least 10%, at least 15%, at least 20%, at least 25%, at least 30%, at least 35%, at least 40%, at least 45%, or at least 50% compared to exercise alone.

In additional embodiments, administration of a composition disclosed herein may increase protein synthesis in subjects with surgery-induced stress. In some aspects, administration of a composition disclosed herein may increase protein synthesis in subjects with surgery-induced stress wherein the composition is administered about 30 minutes, about 1 hour, about 6 hours, about 12 hours, about 24 hours, about 2 days, about 3 days, about 4 days, about 5 days, about 6 days, about 1 week, about 2 weeks, about 1 month, about 6 months, or about 1 year after surgery. In other embodiments, administration of a composition disclosed herein may increase protein synthesis at least 5%, at least 10%, at least 15%, at least 20%, at least 25%, at least 30%, at least 35%, at least 40%, at least 45%, or at least 50% when administered after surgery or injury compared to subjects not administered a composition.

(c) Methods of Promoting Muscle Anabolism

In various embodiments, a method of promoting muscle anabolism may include administration of a composition disclosed herein. In preferred embodiments, a method of promoting muscle anabolism may include oral administration of a composition disclosed herein.

In some aspects, administration of at least about 1 gram to about 11 grams of a composition disclosed herein may promote muscle anabolism in a subject. In various embodiments, administration of a composition disclosed herein comprising one or more EAAs may promote muscle anabolism in a subject. In other aspects, administration of a composition disclosed herein comprising at least about 1 gram to about 11 grams of total EEAs may promote muscle anabolism in a subject. In still other aspects, administration of a composition disclosed herein comprising at least 1 gram, at least 2 grams, at least 3 grams, at least 4 grams, at least 5 grams, at least 6 grams, at least 7 grams, at least 8 grams, at least 9 grams, at least 10 grams, or at least 11 grams of total EEAs may promote muscle anabolism in a subject.

In various embodiments, administration of a composition disclosed herein comprising one or more NEAAs may promote muscle anabolism in a subject. In some aspects, administration of a composition disclosed herein comprising about 0.5 grams to about 2.5 grams total NEAAs may promote muscle anabolism in a subject. In still other aspects, administration of a composition disclosed herein comprising at least about 0.5 grams, about 0.6 grams, about 0.7 grams, about 0.8 grams, about 0.9 grams, about 1.0 grams, about 1.1 grams, about 1.2 grams, about 1.3 grams, about 1.4 grams, about 1.5 grams, about 1.6 grams, about 1.7 grams, about 1.8 grams, about 1.9 grams, about 2.0 grams, about 2.1 grams, about 2.2 grams, about 2.3 grams, about 2.4 grams, or about 2.5 grams total NEAAs may promote muscle anabolism in a subject.

In various embodiments, administration of a composition disclosed herein comprising about 15% NEAAs and about 85% EAAs, about 16% NEAAs and about 84% EAAs, about 17% NEAAs and about 83% EAAs, about 18% NEAAs and about 82% EAAs, about 19% NEAAs and about 81% EAAs, or about 20% NEAAs and about 85% EAAs by weight of total weight of the composition may promote muscle anabolism.

In some embodiments, administration of a composition disclosed herein comprising creatine may promote muscle anabolism. In other embodiments, administration of a composition disclosed herein comprising about 5% to about 10% creatine may promote muscle anabolism in a subject. In some embodiments, administration of a composition disclosed herein comprising creatine and one or more EAAs promotes muscle anabolism compared to administration of a composition consisting of EAAs. In various embodiments, administration of a composition disclosed herein comprising creatine and one or more EAAs promotes muscle anabolism at least 2-fold, at least 4-fold, or at least 5-fold compared to administration of a composition consisting of EAAs.

In some embodiments, administration of a composition comprising one or more intact proteins may promote muscle anabolism in a subject. In some aspects, the intact protein may be whey protein. In other embodiments, administration of a composition disclosed herein comprising about 30% to about 50% total intact dietary protein may promote muscle anabolism in a subject. In some embodiments, administration of a composition disclosed herein comprising intact protein and one or more EAAs may promote muscle anabolism compared to administration of a composition consisting of EAAs. In various embodiments, administration of a composition disclosed herein comprising intact protein and one or more EAAs may promote muscle anabolism by at least 2-fold, at least 4-fold, or at least 5-fold compared to administration of a composition consisting of EAAs.

In various embodiments, administration of a composition comprising one or more nutrient elements may promote muscle anabolism in a subject. In other embodiments, administration of a composition comprising sodium, potassium, or a combination thereof may promote muscle anabolism in a subject. In still other embodiments, administration of a composition comprising one or more excipients may promote muscle anabolism in a subject. In other embodiments, administration of a composition comprising about 8% to about 12% citrulline may promote muscle anabolism in a subject.

In some embodiments, administration of a composition disclosed herein may promote muscle anabolism in a subject by at least 5%, at least 10%, at least 15%, at least 20%, at least 25%, at least 30%, at least 35%, at least 40%, at least 45%, or at least 50% following administration to a subject. In some embodiments, administration of a composition disclosed herein may promote muscle anabolism in a subject at least 5%, at least 10%, at least 15%, at least 20%, at least 25%, at least 30%, at least 35%, at least 40%, at least 45%, or at least 50% compared to exercise alone. In other embodiments, administration of a composition disclosed herein may promote muscle anabolism in a subject by in a dose dependent manner.

In some embodiments, administration of a composition disclosed herein may promote muscle anabolism in a subject by at least 5%, at least 10%, at least 15%, at least 20%, at least 25%, at least 30%, at least 35%, at least 40%, at least 45%, or at least 50% following administration to a young subject. In other embodiments, administration of a composition disclosed herein may promote muscle anabolism in a subject by at least 5%, at least 10%, at least 15%, at least 20%, at least 25%, at least 30%, at least 35%, at least 40%, at least 45%, or at least 50% following administration to a middle-aged subject. In some embodiments, administration of a composition disclosed herein may promote muscle anabolism in a subject by at least 5%, at least 10%, at least 15%, at least 20%, at least 25%, at least 30%, at least 35%, at least 40%, at least 45%, or at least 50% following administration to an elderly subject.

In some embodiments, administration of a composition disclosed herein may promote muscle anabolism in a subject by at least 5%, at least 10%, at least 15%, at least 20%, at least 25%, at least 30%, at least 35%, at least 40%, at least 45%, or at least 50% following administration to a underweight subject. In other embodiments, administration of a composition disclosed herein may promote muscle anabolism in a subject by at least 5%, at least 10%, at least 15%, at least 20%, at least 25%, at least 30%, at least 35%, at least 40%, at least 45%, or at least 50% following administration to a subject of normal weight. In still other embodiments, administration of a composition disclosed herein may promote muscle anabolism in a subject by at least 5%, at least 10%, at least 15%, at least 20%, at least 25%, at least 30%, at least 35%, at least 40%, at least 45%, or at least 50% following administration to an overweight subject. In some embodiments, administration of a composition disclosed herein may promote muscle anabolism in a subject by at least 5%, at least 10%, at least 15%, at least 20%, at least 25%, at least 30%, at least 35%, at least 40%, at least 45%, or at least 50% following administration to an obese subject.

In other embodiments, administration of a composition disclosed herein may promote muscle anabolism in a subject by at least 5%, at least 10%, at least 15%, at least 20%, at least 25%, at least 30%, at least 35%, at least 40%, at least 45%, or at least 50% following administration to a subject with a condition wherein the condition may be cardiovascular disease, hypertension, osteoporosis, diabetes, metabolic disorder, or cancer.

In some embodiments, administration of a composition disclosed herein may promote muscle anabolism in a subject by at least 5%, at least 10%, at least 15%, at least 20%, at least 25%, at least 30%, at least 35%, at least 40%, at least 45%, or at least 50% following administration to a stressed subject. In other aspects, administration of a composition disclosed herein may promote muscle anabolism in subjects with injury-induced stress. In still other aspects, administration of a composition disclosed herein may promote muscle anabolism in subjects with inactivity-induced stress.

In other aspects, administration of a composition disclosed herein may promote muscle anabolism in subjects with immobility-induced stress.

In still other aspects, administration of a composition disclosed herein may promote muscle anabolism in subjects with exercise-induced stress. In other embodiments, administration of a composition disclosed herein to a subject following an exercise regimen may promote muscle anabolism at least 5%, at least 10%, at least 15%, at least 20%, at least 25%, at least 30%, at least 35%, at least 40%, at least 45%, or at least 50% compared to exercise alone.

In additional embodiments, administration of a composition disclosed herein may promote muscle anabolism in subjects with surgery-induced stress. In some aspects, administration of a composition disclosed herein may promote muscle anabolism in subjects with surgery-induced stress wherein the composition is administered about 30 minutes, about 1 hour, about 6 hours, about 12 hours, about 24 hours, about 2 days, about 3 days, about 4 days, about 5 days, about 6 days, about 1 week, about 2 weeks, about 1 month, about 6 months, or about 1 year after surgery. In other embodiments, administration of a composition disclosed herein may promote muscle anabolism at least 5%, at least 10%, at least 15%, at least 20%, at least 25%, at least 30%, at least 35%, at least 40%, at least 45%, or at least 50% when administered after surgery compared to subjects not administered a composition.

(d) Methods of Preserving Muscle Mass and Strength and Minimizing or Preventing Muscle Atrophy In various embodiments, a method of preserving muscle mass and/or strength and/or minimizing or preventing muscle atrophy may include administration of a composition disclosed herein. In preferred embodiments, a method of preserving muscle mass and/or strength may include oral administration of a composition disclosed herein.

In some aspects, administration of at least about 1 gram to about 20 grams of a composition disclosed herein may preserve muscle mass and/or strength in a subject. In various embodiments, administration of a composition disclosed herein comprising one or more EAAs may preserve muscle mass and/or strength in a subject. In other aspects, administration of a composition disclosed herein comprising at least about 1 gram to about 20 grams of total EAAs may preserve muscle mass and/or strength in a subject. In still other aspects, administration of a composition disclosed herein comprising at least 1 gram, at least 2 grams, at least 3 grams, at least 4 grams, at least 5 grams, at least 6 grams, at least 7 grams, at least 8 grams, at least 9 grams, at least 10 grams, at least 11 grams, at least 10 grams, at least 11 gram, at least 12 grams, at least 13 grams, at least 14 grams, at least 15 grams, at least 16 grams, at least 17 grams, at least 18 grams, at least 19 grams, or at least 20 grams of total EAAs may preserve muscle mass and/or strength in a subject.

In various embodiments, administration of a composition disclosed herein comprising one or more NEAAs may preserve muscle mass and/or strength in a subject. In some aspects, administration of a composition disclosed herein comprising about 0.5 grams to about 5 grams total NEAAs may preserve muscle mass and/or strength in a subject. In still other aspects, administration of a composition disclosed herein comprising at least about 0.5 grams, about 0.6 grams, about 0.7 grams, about 0.8 grams, about 0.9 grams, about 1.0 grams, about 1.1 grams, about 1.2 grams, about 1.3 grams, about 1.4 grams, about 1.5 grams, about 1.6 grams, about 1.7 grams, about 1.8 grams, about 1.9 grams, about 2.0 grams, about 2.1 grams, about 2.2 grams, about 2.3 grams, about 2.4 grams, about 2.5 grams, about 2.6 grams, about 2.7 grams, about 2.8 grams, about 2.9 grams, about 3.0 grams, about 3.1 grams, about 3.2 grams, about 3.3 grams, about 3.4 grams, about 3.5 grams, about 3.6 grams, about 3.7 grams, about 3.8 grams, about 3.9 grams, about 4.0 grams, about 4.1 grams, about 4.2 grams, about 4.3 grams, about 4.4 grams, about 4.5 grams, about 4.6 grams, about 4.7 grams, about 4.8 grams, about 4.9 grams, or about 5.0 grams total NEAAs may preserve muscle mass and/or strength in a subject.

In various embodiments, administration of a composition disclosed herein comprising about 15% NEAAs and about 85% EAAs, about 16% NEAAs and about 84% EAAs, about 17% NEAAs and about 83% EAAs, about 18% NEAAs and about 82% EAAs, about 19% NEAAs and about 81% EAAs, about 20% NEAAs and about 85% EAAs, or about 25% NEAAs and about 75% EAAs by weight of total weight of the composition may preserve muscle mass and/or strength.

In some embodiments, administration of a composition disclosed herein comprising creatine may preserve muscle mass and/or strength. In other embodiments, administration of a composition disclosed herein comprising about 5% to about 10% creatine may preserve muscle mass and/or strength when administered with free EAAs. In some embodiments, administration of a composition disclosed herein comprising creatine and one or more EAAs may preserve muscle mass and/or strength compared to administration of a composition consisting of EAAs. In various embodiments, administration of a composition disclosed herein comprising creatine and one or more EAAs nay preserve muscle mass and/or strength at least 2-fold compared to administration of a composition consisting of EAAs.

In some embodiments, administration of a composition comprising one or more intact proteins may preserve muscle mass and/or strength in a subject. In some aspects, the intact protein may be whey protein. In other embodiments, administration of a composition disclosed herein comprising about 30% to about 50% total intact dietary protein may preserve muscle mass and/or strength in a subject. In some embodiments, administration of a composition disclosed herein comprising intact protein and one or more EAAs may preserve muscle mass and/or strength compared to administration of a composition consisting of EAAs. In various embodiments, administration of a composition disclosed herein comprising intact protein and one or more EAAs may preserve muscle mass and/or strength by at least 2-fold compared to administration of a composition consisting of EAAs.

In still other embodiments, administration of a composition comprising one or more excipients may preserve muscle mass and/or strength in a subject. In other embodiments, administration of a composition comprising about 8% to about 12% citrulline may preserve muscle mass and/or strength in a subject.

In some embodiments, administration of a composition disclosed herein may preserve muscle mass and/or strength in a subject by at least 5%, at least 10%, at least 15%, at least 20%, at least 25%, at least 30%, at least 35%, at least 40%, at least 45%, at least 50%, at least 55%, at least 60%, at least 65%, or at least 70% following administration to a subject. In some embodiments, administration of a composition disclosed herein may preserve muscle mass and/or strength in a subject at least 5%, at least 10%, at least 15%, at least 20%, at least 25%, at least 30%, at least 35%, at least 40%, at least 45%, at least 50%, at least 55%, at least 60%, at least 65%, or at least 70% compared to exercise alone. In other embodiments, administration of a composition disclosed herein may preserve muscle mass and/or strength in a subject by in a dose dependent manner.

In some embodiments, administration of a composition disclosed herein may preserve muscle mass and/or strength in a subject by at least 5%, at least 10%, at least 15%, at least 20%, at least 25%, at least 30%, at least 35%, at least 40%, at least 45%, or at least 50% following administration to an elderly subject.

In some embodiments, administration of a composition disclosed herein may preserve muscle mass and/or strength in a subject by at least 5%, at least 10%, at least 15%, at least 20%, at least 25%, at least 30%, at least 35%, at least 40%, at least 45%, or at least 50% following administration to a underweight subject. In other embodiments, administration of a composition disclosed herein may preserve muscle mass and/or strength in a subject by at least 5%, at least 10%, at least 15%, at least 20%, at least 25%, at least 30%, at least 35%, at least 40%, at least 45%, or at least 50% following administration to an overweight subject. In some embodiments, administration of a composition disclosed herein may preserve muscle mass and/or strength in a subject by at least 5%, at least 10%, at least 15%, at least 20%, at least 25%, at least 30%, at least 35%, at least 40%, at least 45%, or at least 50% following administration to an obese subject.

In other embodiments, administration of a composition disclosed herein may preserve muscle mass and/or strength in a subject by at least 5%, at least 10%, at least 15%, at least 20%, at least 25%, at least 30%, at least 35%, at least 40%, at least 45%, or at least 50% following administration to a subject with a condition wherein the condition may be cardiovascular disease, hypertension, osteoporosis, diabetes, metabolic disorder, or cancer.

In some embodiments, administration of a composition disclosed herein may preserve muscle mass and/or strength in a subject by at least 5%, at least 10%, at least 15%, at least 20%, at least 25%, at least 30%, at least 35%, at least 40%, at least 45%, or at least 50% following administration to a stressed subject. In other aspects, administration of a composition disclosed herein may preserve muscle mass and/or strength in subjects with injury-induced stress. In still other aspects, administration of a composition disclosed herein may preserve muscle mass and/or strength in subjects with inactivity-induced stress. In other aspects, administration of a composition disclosed herein may preserve muscle mass and/or strength in subjects with immobility-induced stress.

In additional embodiments, administration of a composition disclosed herein may preserve muscle mass and/or strength in subjects with surgery-induced stress. In some aspects, administration of a composition disclosed herein may preserve muscle mass and/or strength in subjects with surgery-induced stress wherein the composition is administered about 30 minutes, about 1 hour, about 6 hours, about 12 hours, about 24 hours, about 2 days, about 3 days, about 4 days, about 5 days, about 6 days, about 1 week, about 2 weeks, about 1 month, about 6 months, or about 1 year after surgery. In other embodiments, administration of a composition disclosed herein may preserve muscle mass and/or strength at least 5%, at least 10%, at least 15%, at least 20%, at least 25%, at least 30%, at least 35%, at least 40%, at least 45%, or at least 50% when administered after surgery compared to subjects not administered a composition.

EXAMPLES

The following examples are included to demonstrate various embodiments of the present disclosure. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Figure 1:
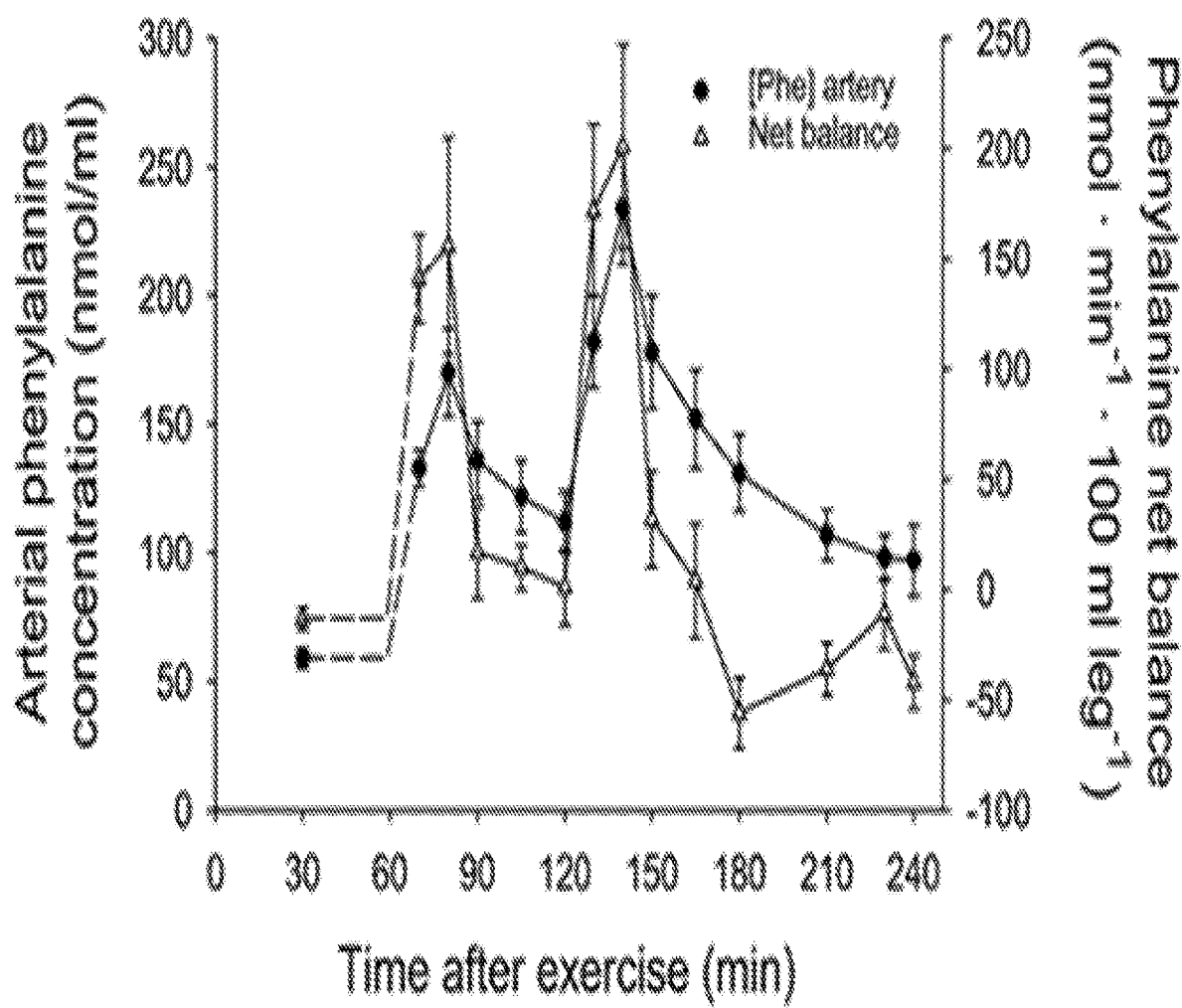
FIG. 1 depicts a graph showing arterial phenylalanine concentration and net phenylalanine balance across the leg in normal human volunteers during the recovery period after a resistance exercise bout wherein a dose of 6 grams of essential amino acids (EAAs) was administered 1 hour after resistance exercise and 2 hours after resistance exercise. Net phenylalanine balance across the leg reflects the net balance between protein synthesis and breakdown in skeletal muscle. Error bars represent standard error of mean (SE) assessed via ANOVA. (n=6)

Six healthy untrained subjects received a primed constant infusion of L-[$^2$H$_5$]phenylalanine and L-[1-$^{13}$C]leucine. Next, the subjects performed resistance exercises for about 40 minutes. Subjects received a dose of 6 grams of orally administered essential amino acids (EAAs) in the profile described herein 1 hour after resistance exercise followed by another of dose of 6 grams of EAAs 2 hours after resistance exercise. Blood samples from the femoral artery and vein in addition to biopsies from vastus lateralis muscle were collected at 30, 70, 80, 90, 105, 130, 140, 150, 165, 180, 210, 220, and 240 minutes after completion of the resistance exercise regimen. Arterial EAA concentrations increased several-fold after each EAA dose where the EAA concentration a t=30 minutes was used at the baseline measurement. Because phenylalanine is neither produced nor metabolized in muscle, net phenylalanine balance reflects net protein synthesis, provided there are no significant changes in the free intracellular pool of phenylalanine. As such, net muscle protein balance (NB) was calculated as follows: (phenylalanine arterial concentration−phenylalanine venous concentration)×blood flow. NB increased proportionally more than arterial EAA concentration in response to each EAA dose. NB returned rapidly to basal values when arterial EAA concentrations decreased. Area under the curve for net phenylalanine uptake above basal value was similar for the first hour after each EAA dose (67±17 mg/leg vs. 77±20 mg/leg, respectively) (FIG. 1).

The conclusion from this study was that a 6 g dose of the EAA formulation provided a rapid and significant gain in net protein balance, but that the effect was very transient. These results provided support for the notion that a combination of EAAs and protein would capitalize on both the initial rapid response to the EAAs and a more prolonged response to a protein component.

Example 2

Figure 2:
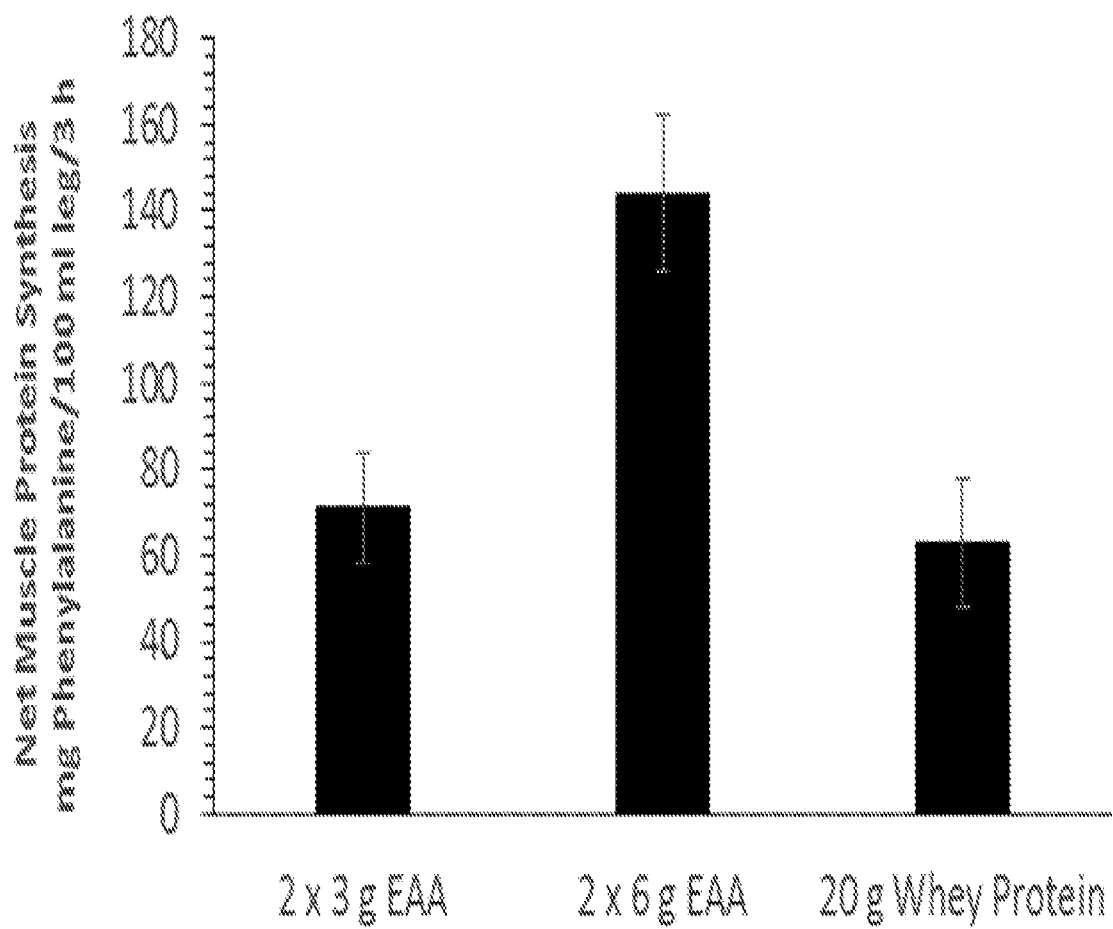
FIG. 2 depicts a graph showing the total rate of net muscle protein synthesis in human subjects over a 3-hour recovery period after a resistance exercise bout wherein subjects were administered either a dose of 6 grams of essential amino acids (EAAs) 1 hour after resistance exercise and 2 hours after resistance exercise, a dose of 3 grams of EAAs 1 hour after resistance exercise and 2 hours after resistance exercise, or a dose of 20 grams of whey protein 1 hour after resistance exercise. Error bars represent standard error of mean (SE) assessed via ANOVA.

A total of 22 healthy untrained subjects received a primed constant infusion of L-[$^2$H$_5$]phenylalanine and L-[1-$^{13}$C] leucine. Next, the subjects performed resistance exercises for about 40 minutes. Subjects received either: (1) a dose of 6 grams of orally administered essential amino acids (EAAs) 1 hour after resistance exercise followed by another of dose of 6 grams of EAAs 2 hours after resistance exercise (n=8); (2) a dose of 3 grams of orally administered essential amino acids (EAAs) 1 hour after resistance exercise followed by another of dose of 3 grams of EAAs 2 hours after resistance exercise (n=6); or (3) a dose of 20 grams of whey protein 1 hour after resistance exercise (n=8). Blood samples from the femoral artery and vein in addition to biopsies from vastus lateralis muscle were collected at 30, 70, 80, 90, 105, 130, 140, 150, 165, and 180 minutes after completion of the resistance exercise regimen. NB was calculated from samples to determine total net muscle protein synthesis over 3 hours post exercise. Total net muscle protein synthesis following 2 doses of 6 grams of EAAs was almost double total net muscle protein synthesis following 2 doses of 3 grams of EAAs and whey protein (FIG. 2).

The result and data demonstrate that: a small dose of EAAs can effectively stimulate net muscle gain; there is a dose-response to EAA consumption; and that while whey protein can also stimulate muscle protein synthesis, the response is considerably less than the response to the EAAs. The results also demonstrate that if the EAA levels in the blood are increased over a sustained period of time (i.e. by the two doses an hour apart), the anabolic effect on net muscle gain is also prolonged. While the prolongation of the EAA effect was sustained in this example by multiple doses of EAAs, the results also supported the notion that the combination of EAAs and whey protein may effectively prolong the EAA effect as well.

Example 3

Young healthy individuals were confined to complete bed rest for 28 days. Major outcome measures included mixed muscle fractional synthetic rate (FSR), phenylalanine net balance, lean leg mass, and leg extension strength. On day 1 and 28 of bed rest, vastus lateralis muscle biopsies and femoral arterio-venous blood samples were obtained during a primed constant infusion of I-[ring-(2)H(5)]phenylalanine. Net balance and FSR were calculated over 16 hours, during which the control group (CON) received a nutritionally mixed meal every 5 hour (0830, 1330, and 1830 hr). The experimental group (EAA) also consumed 16.5 grams essential amino acids (EAAs) in the profile described herein and 30 grams carbohydrate (1100, 1600, and 2100 hr). The dietary regimen was maintained during bed rest.

Figure 3:
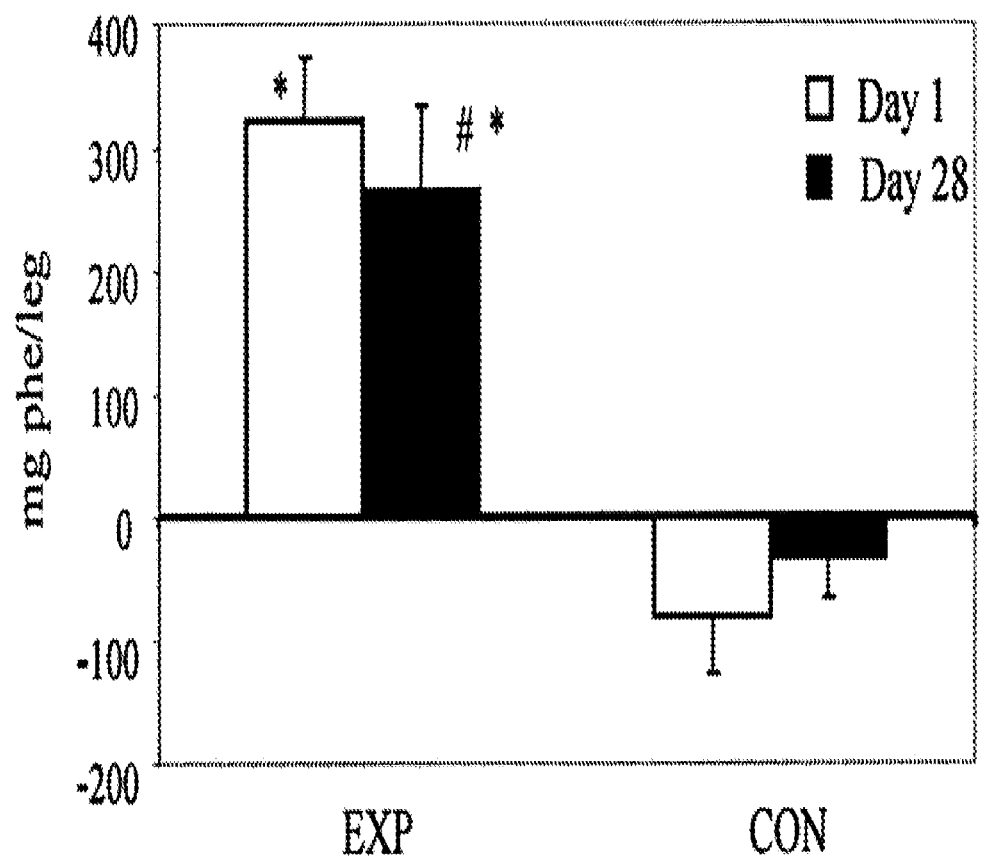
FIG. 3 depicts a graph showing phenylalanine balance representing net muscle gain or loss across the leg of young, healthy subjects on for 16 h on day 1 and day 28 of complete bed rest. The control (CON) and experimental (EAA) groups received three nutritionally balanced mixed meals every 5 hours over the 16-hour experimental period and the EAA group also consumed 3 doses of a formulation of 16.5 grams each of essential amino acids and 30 grams carbohydrate every 5 hours. Error bars represent standard error of mean (SE) assessed via a standard student t-test.

FSR was higher in the EAA+ group on day 1 (EXP, 0.099+/-0.008%/h; CON: 0.075+/-0.005%/h) and day 28 (EXP, 0.093+/-0.006%/h; CON, 0.055+/-0.007%/h). Leg phenylalanine balance, a direct reflection of net muscle protein synthesis, was also significantly higher in the EAA group on both days 1 and day 28 (FIG. 3).

Figure 4:
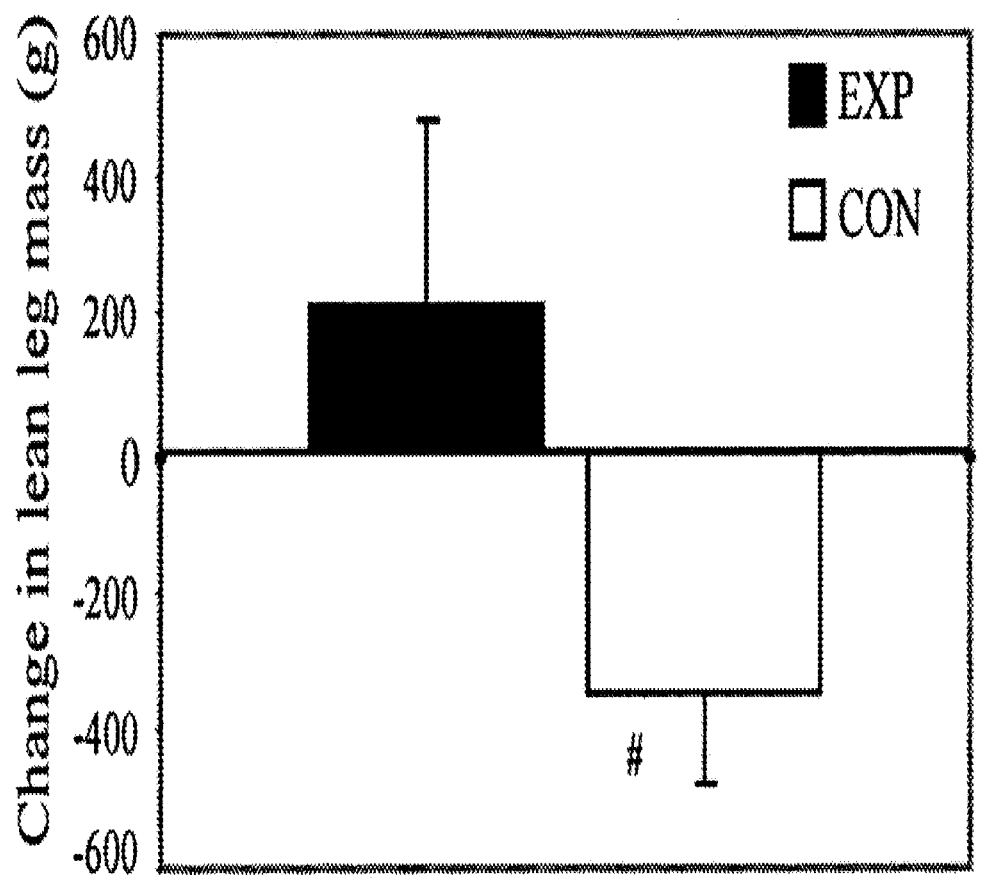
FIG. 4 depicts a graph showing change in leg lean mass (grams) (reflecting largely muscle) after 28 days bed rest in young, healthy subjects wherein the control group (CON)

Lean leg mass was maintained throughout bed rest in the EXP group (+0.2+/-0.3 kg), but fell in the CON group (-0.4+/-0.1 kg) (FIG. 4).

Strength loss was more pronounced in the CON group (EXP, -8.8+/-1.4 kg; CON, -17.8+/-4.4 kg).

The results of this study confirmed that EAAs and carbohydrate supplementation may represent a viable intervention for individuals at risk of sarcopenia due to immobility or prolonged bed rest. The results also confirmed the validity of the isotopic determination of net protein synthesis as a predictor of changes in lean body mass over time in completely controlled conditions. The results did not, however, distinguish between the EAA effect and the carbohydrate effect, or if a combination of glucose and EAAs provided a synergistic effect that exceeded the sum of their individual anabolic effects.

Example 4

Two groups of eight subjects performed a resistance exercise bout (10 sets of 8 repetitions of leg presses at 80% of 1-repetition maximum) before bed rest for 4 hours. One group (CHO) received a drink consisting of 100 grams of carbohydrates 1 hour post-exercise. The other group (Pla) received a non-caloric placebo drink. Leg amino acid metabolism was determined by infusion of 2H5- or 13C6-labeled phenylalanine, sampling from femoral artery and vein, and muscle biopsies from vastus lateralis. Drink intake did not affect arterial insulin concentration in Pla, whereas insulin increased several times after the drink in CHO (P<0.05 vs. Pla). Arterial phenylalanine concentration fell slightly after the drink in CHO. Net muscle protein balance between synthesis and breakdown did not change in Pla, whereas it improved in CHO from -17+/-3 nmol·ml(-1)·100 ml leg(-1) before drink to an average of -4+/-4 and 0+/-3 nmol·ml(-1)·100 ml leg(-1) during the second and third hour after the drink, respectively (P<0.05 vs. Pla during last hour). The improved net balance in CHO was due primarily to a progressive decrease in muscle protein breakdown. The results demonstrated that ingestion of carbohydrates improved net leg protein balance after resistance exercise; however, the effect was minor and delayed compared with the previously reported effect of ingestion of amino acids. The results of this study demonstrated that inclusion of CHO would be unlikely to add significant anabolic benefit to a composition of EAAs.

Example 5

The net gain of body protein following either consumption of the EAA/protein composition described herein or a whey protein recovery product (Gatorade Recover Whey Protein) in an amount equal to the high dose of the EAA/protein composition was determined for 16 subjects. The demographics of said subjects are provided in Table 1.

TABLE 1

| Subject demographics | | |
|---|---|---|
| | Low & High EAA | Whey Protein |
| Subject number (Male/Female) | 8 (3/5) | 8 (4/4) |
| Age, yr | 21.4 ± 0.5 | 26.9 ± 2.0 |
| Body weight (kg) | 73.8 ± 4.8 | 76.2 ± 3.1 |
| Body mass idex (kg/m$^2$) | 24.6 ± 0.8 | 25.7 ± 1.6 |
| Lean body mass | 51.6 ± 4.9 | 49.5 ± 2.6 |
| Fat mass, % | 21.1 ± 2.2 | 24.8 ± 4.1 |

The protocol involved a two-period, stable isotope (Cambridge Isotope Labs, Tewksbury, Mass.) infusion study: a 4.5-hour basal fasted period and 4-hour post-meal period (total 8.5-hour time period). The principal endpoint was the total anabolic response (whole body protein synthesis minus breakdown, NB) and the secondary end points were rates of protein synthesis and breakdown. There were two distinct arms of the protocol. Arm 1 consisted of a group of subjects who participated in a randomized, single blind cross-over (two stable isotope studies). In this group, two doses of the EAA/protein study composition were tested (6.3 grams and 12.6 grams), with a ≥one week washout period between stable isotope studies. Arm 2 consisted of a group of subjects (with similar gender composition) who participated in one stable isotope study consisting of a basal period and then 4 hours following ingestion of 12.6 grams whey protein product. The composition of study products is provided in tables 2 and 3.

TABLE 2

| EAA/protein study composition (6.3 g serving) | |
|---|---|
| EAA | 3.2 g |
| Creatine | 0.5 g |
| Whey protein | 2.3 g |
| Flavoring | 0.3 |
| Amino Acids (% of total EEAs) | |

TABLE 2-continued

EAA/protein study composition (6.3 g serving)

| | |
|---|---|
| Histidine | 10 |
| Isoleucine | 10 |
| Leucine | 20 |
| Lysine | 19 |
| Methionine | 3 |
| Phenylalanine | 12 |
| Threonine | 16 |
| Valine | 10 |

TABLE 3

Gatorade Recover Whey Protein (12.6 g serving)

| | |
|---|---|
| Protein | 8.9 g |
| Fat | 0.7 g |
| Carbohydrate | 1.8 g |
| Flavoring | 1.2 g |

Subjects and investigators were blinded to the extent feasible, given that different beverages looked and tasted different. Since an individual has no conscious control over their rate of protein synthesis, total blinding is of little concern. Nonetheless, subjects were not told which dose of the product they were consuming. If a subject were to consume the whey protein, the subject knew what it was since they were only participating in one study. A stable tracer protocol was performed according to the schematic show in FIG. 5.

Protein synthesis, breakdown and NB were determined using primed-constant infusions of L-[ring 2H5]-phenylalanine and L-[ring-2H2-tyrosine stable isotope tracers. In each study there was a 4.5 hours basal (post-absorptive) phase, followed by ingestion of the study product and following the response for the next 4 hours (total of 8.5-hour study). Samples were analyzed for stable isotope enrichment by gas chromatography mass spectrometry.

Plasma Amino Acid Concentrations.

Total plasma EAA concentration in the basal state and following ingestion of one of three beverages is shown in FIG. 6. The total EAA concentration following consumption of the EAA/protein beverage was directly related to the dose of study product. Even the low-dose EAA/protein product caused a significantly greater increase in EAA concentration than whey protein. Perhaps more importantly, plasma leucine increased to significantly higher values in both EAA/protein doses than the whey protein product, even though the amount of leucine ingested in the whey protein was comparable to the high dose of EAA/protein, and almost twice as great in the amount of leucine ingested in the low-dose EAA/protein (FIG. 6). This is important because a rationale for EAA formulations with higher proportions of leucine than in the EAA/protein formulation is that the peak leucine level is the signal to activate the process of protein synthesis. The results shown in FIG. 6 demonstrate that a small amount of leucine in the free form can raise leucine concentration in plasma sufficiently to elicit a stimulation of protein synthesis, while at the same time enabling greater proportions of the other EAAs in the EAA/protein formulation described herein.

The second important point evident from inspection of FIG. 6 is that the EAA and leucine concentrations remain higher after consumption of the EAA/protein mixture than following ingestion of whey protein alone. This is due to the unique proportions of EAAs and protein in the composition. The free EAAs are completely and rapidly digested, accounting for the rapid increase in plasma EAA and leucine concentrations. However, just as the levels rise rapidly after consumption of free EAAs, they would also normally fall rapidly as well (see FIG. 1). In the composition containing EAAs plus protein, the slower-absorbed EAAs from digestion of the protein mixture sustain the increase in concentrations initially caused by the free EAAs. The interaction between the EAAs and protein are dependent on the exact amounts of one relative to the other.

All three products increased net muscle protein balance (NB)(FIG. 7). The total gain in NB was greatest (17.0+/−0.17 g protein) in the group consuming 12.6 g of the EAA/protein composition (statistically significantly greater than the other two groups, $p<0.01$). The increase in NB in the group consuming 6.3 grams of the EAA/protein composition was 8.2+/−0.3 g protein, which was significantly greater than the gain in NB in the group receiving 12.6 grams of the whey protein product (3.99+/−0.17 gram protein). The greater increases in NB with the EAA/protein compositions were due to both greater increases in the rate of protein synthesis and greater suppression of protein breakdown as compared to the whey protein product. When normalized for the amount of product given, the EAA/protein composition was more than 4 times as effective per gram of product given than whey protein (FIG. 7).

The remarkable result was that in the case of the EAA/protein composition the net gain in body protein was 20% greater than the amount of product given. In contrast, whey protein resulted in a gain of approximately 30% of the amount consumed (FIG. 7).

The remarkable efficiency of the EAA/protein composition was greater than predicted from the examples cited above in which either EAAs or whey protein were given independently. The unique anabolic effect of the EAA/protein mixture occurred in part because stimulation of protein synthesis by consumption of EAAs results in more efficient recycling of non-essential amino acids back into protein because all amino acids are necessary to produce a complete protein. However, increased recycling of non-essential amino acids alone cannot explain the remarkable efficiency of the EAA/protein composition. In addition to a greater efficiency in protein synthesis, protein breakdown was greatly suppressed in the groups consuming the EAA/protein composition. This unexpected response was not previously observed in the studies cited above in which either EAAs or protein were given independently. Consistent with previous examples described above, protein breakdown was not significantly suppressed in the group given the whey protein product (FIG. 7), nor was protein breakdown suppressed when 6 g of only EAAs were given (Example 1 above). Suppression of protein breakdown played an important role in making the anabolic response to the EAA/protein composition greater than the whey protein product, and previous results would not have predicted the reduction in protein breakdown caused by the combination of EAAs and protein. The only explanation for the remarkable efficiency of the EAA/protein composition is that the EAAs, creatine monohydrate and intact protein had a synergistic effect that exceeded the sum of their individual effects.

Thus, there has been described a composition and method of using the composition to stimulate growth, repair and maintenance of muscle. It is apparent to those skilled in the art, however, that many changes, clarifications, modifications, other uses, and applications for the composition and method of using are possible, and also such changes, variations, modifications, other uses, and application which do not depart from the spirit and scope of the invention are deemed to be covered by the invention, which is limited only by the claims which follow.

What is claimed is:

1. A composition to stimulate protein synthesis comprising an amount of free essential amino acids (EAAs) composition, wherein the EAAs composition consists of from about 8% to about 12% L-histidine, from about 9% to about 11% L-isoleucine, from about 18% to about 22% L-leucine, from about 16% to about 23% L-lysine, from about 2% to about 5% L-methionine, from about 12% to about 16% L-phenylalanine, from about 9% to about 12% L-valine, and from about 14% to about 18% L-threonine of the EAAs composition by weight; and an amount of whey protein from 30-50% of the composition, and an amount of creatine monohydrate from 6-10% of total weight of active components.

2. The composition of claim 1, further includes an amount of citrulline, wherein the amount is from 8% to about 12% of the composition.

3. The composition of claim 1, where the composition is in a powder form or a beverage.

4. A capsule comprising: a core material comprising the amino acids according to claim 1; an intact protein; and a shell wall of material, selected from the group consisting of soft gelatin, hard gelation, and a polymer, that encapsulates the core material.

5. The capsule of claim 4, wherein the core material further comprises at least one excipient.

6. The capsule of claim 4, wherein the core material further comprises an agent selected from the group consisting of: synephrine, citrus aurantium extract, phenylpropanolamine, caffeine, aspirin, and a combination thereof, and/or the group consisting of sibutramine, phentermine, diethylproprion, mazindol, and phendimetrazine.

7. The composition of claim 1, wherein the composition is incorporated into a food product.

8. The composition of claim 1, wherein the food product is selected from the group consisting of: a drink, a frozen treat bar, a snack bar and a bakery product.

* * * * *